United States Patent
Bayasi et al.

(10) Patent No.: US 10,548,499 B2
(45) Date of Patent: *Feb. 4, 2020

(54) MEDICAL DEVICE AND METHOD FOR DETECTING A VENTRICULAR ARRHYTHMIA EVENT

(71) Applicant: Khalifa University of Science and Technology, Abu Dhabi (AE)

(72) Inventors: Nourhan Yahya Bayasi, Ajman (AE); Temesghen Tekeste Habte, Asmara (ER); Hani Hasan Mustafa Saleh, Abu Dhabi (AE); Ahsan Habib Khandoker, Abu Dhabi (AE); Mohammed Ismail Elnaggar, Abu Dhabi (AE)

(73) Assignee: Khalifa University of Science and Technology, Abu Dhabi (AE)

( * ) Notice: Subject to any disclaimer, the term of this patent is extended or adjusted under 35 U.S.C. 154(b) by 209 days.

This patent is subject to a terminal disclaimer.

(21) Appl. No.: 15/616,069

(22) Filed: Jun. 7, 2017

(65) Prior Publication Data

US 2017/0265768 A1 Sep. 21, 2017

Related U.S. Application Data

(63) Continuation of application No. 14/926,483, filed on Oct. 29, 2015, now Pat. No. 9,717,438.
(Continued)

(51) Int. Cl.
*A61B 5/0464* (2006.01)
*A61B 5/0468* (2006.01)
(Continued)

(52) U.S. Cl.
CPC .......... *A61B 5/0468* (2013.01); *A61B 5/0245* (2013.01); *A61B 5/02405* (2013.01);
(Continued)

(58) Field of Classification Search
CPC ... A61B 5/024; A61B 5/02405; A61B 5/0245; A61B 5/0255; A61B 5/04012;
(Continued)

(56) References Cited

U.S. PATENT DOCUMENTS

| 5,277,189 A | * | 1/1994 | Jacobs | A61B 5/0245 600/508 |
| 5,758,654 A | * | 6/1998 | Burton-Krahn | A61B 5/0452 600/517 |

(Continued)

OTHER PUBLICATIONS

N. Bayasi, T. Tekeste, H. Saleh, A. Khandoker, B. Mohammad and M. Ismail, "Adaptive technique for P and T wave delineation in electrocardiogram signals," 2014 36th Annual International Conference of the IEEE Engineering in Medicine and Biology Society, Chicago, IL, 2014, pp. 90-93.*

(Continued)

*Primary Examiner* — Eugene T Wu
(74) *Attorney, Agent, or Firm* — Withrow & Terranova, P.L.L.C.

(57) ABSTRACT

A medical device and method for detecting a ventricular arrhythmia event is disclosed. The medical device includes input circuitry configured to receive an electrocardiogram (ECG) signal and processing circuitry coupled to the input circuitry that is configured to identify fiducial points within the ECG signal. Feature extraction circuitry coupled to the processing circuitry is configured to determine interval variability between the fiducial points. Machine learning circuitry is coupled to the feature extraction circuitry and is configured to detect ventricular arrhythmia based on the interval variability between the fiducial points.

16 Claims, 15 Drawing Sheets

Related U.S. Application Data

(60) Provisional application No. 62/069,975, filed on Oct. 29, 2014, provisional application No. 62/074,409, filed on Nov. 3, 2014.

(51) Int. Cl.

| | | |
|---|---|---|
| *A61B 5/0428* | (2006.01) | |
| *A61B 5/0245* | (2006.01) | |
| *A61B 5/00* | (2006.01) | |
| *A61B 5/04* | (2006.01) | |
| *A61B 5/024* | (2006.01) | |
| *A61B 5/0402* | (2006.01) | |
| *A61B 5/0456* | (2006.01) | |

(52) U.S. Cl.
CPC ........ *A61B 5/0402* (2013.01); *A61B 5/04012* (2013.01); *A61B 5/0428* (2013.01); *A61B 5/0456* (2013.01); *A61B 5/0464* (2013.01); *A61B 5/7264* (2013.01)

(58) Field of Classification Search
CPC . A61B 5/0402; A61B 5/0432; A61B 5/04325; A61B 5/0452; A61B 5/046; A61B 5/0464; A61B 5/0468; A61B 5/0472; A61B 5/7235; A61B 5/7246; A61B 5/7264; A61B 5/7267; A61B 5/7282
See application file for complete search history.

(56) References Cited

U.S. PATENT DOCUMENTS

| | | | | |
|---|---|---|---|---|
| 7,155,282 | B1* | 12/2006 | Min | A61B 5/0452 607/28 |
| 7,610,086 | B1 | 10/2009 | Ke et al. | |
| 9,717,438 | B2 | 8/2017 | Bayasi et al. | |
| 2005/0004481 | A1* | 1/2005 | Xue | A61B 5/02405 600/509 |
| 2006/0116733 | A1* | 6/2006 | Gunderson | A61N 1/3704 607/27 |
| 2007/0203418 | A1* | 8/2007 | Starc | A61B 5/04525 600/509 |
| 2007/0276274 | A1 | 11/2007 | Kawada et al. | |
| 2008/0300497 | A1* | 12/2008 | Krause | A61B 5/0031 600/515 |
| 2010/0217144 | A1* | 8/2010 | Brian | A61B 5/0452 600/523 |
| 2015/0032990 | A1 | 1/2015 | Markovic et al. | |
| 2016/0120431 | A1 | 5/2016 | Habte et al. | |
| 2017/0095175 | A1* | 4/2017 | Allavatam | A61B 5/0472 |

OTHER PUBLICATIONS

Pan and Tompkins. "A Real-Time QRS Detection Algorithm". IEEE Transactions on Biomedical Engineering, vol. BME-32, No. 3, Mar. 1985.*
J. P. Martinez, R. Almeida, S. Olmos, A. P. Rocha and P. Laguna, "A wavelet-based ECG delineator: evaluation on standard databases," in IEEE Transactions on Biomedical Engineering, vol. 51, No. 4, pp. 570-581, Apr. 2004.*
N. Bayasi, T. Tekeste, H. Saleh, B. Mohammad and M. Ismail, "A 65-nm low power ECG feature extraction system," 2015 IEEE International Symposium on Circuits and Systems (ISCAS), Lisbon, 2015, pp. 746-749.*
Final Office Action for U.S. Appl. No. 14/926,554, dated Sep. 27, 2017, 12 pages.
Zhang, Xu-Sheng et al., "Detecting Ventricular Tachycardia and Fibrillation by Complexity Measure," IEEE Transactions on Biomedical Engineering, vol. 46, No. 5, 1999, pp. 548-555.
Zong, W. et al., "A QT Interval Detection Algorithm Based on ECG Curve Length Transform," Computers in Cardiology, vol. 33, Oct. 2006, IEEE, pp. 377-380.
Zong, W. et al., "A Robust Open-source Algorithm to Detect Onset and Duration of QRS Complexes," Computers in Cardiology, vol. 30, 2003, pp. 737-740.
Zong, W. et al., "Automated ECG Rhythm Analysis Using Fuzzy Reasoning," Computers in Cardiology, vol. 25, 1998, pp. 69-72.
Non-Final Office Action for U.S. Appl. No. 14/926,483, dated Sep. 28, 2016, 8 pages.
Final Office Action for U.S. Appl. No. 14/926,483, dated Jan. 20, 2017, 7 pages.
Notice of Allowance for U.S. Appl. No. 14/926,483, dated Mar. 24, 2017, 11 pages.
Corrected Notice of Allowance for U.S. Appl. No. 14/926,483, dated Apr. 28, 2017, 4 pages.
Non-Final Office Action for U.S. Appl. No. 14/926,554, dated Sep. 28, 2016, 14 pages.
Final Office Action for U.S. Appl. No. 14/926,554, dated Jan. 26, 2017, 11 pages.
Advisory Action for U.S. Appl. No. 14/926,554, dated Apr. 3, 2017, 3 pages.
Non-Final Office Action for U.S. Appl. No. 14/926,554, dated Jun. 15, 2017, 12 pages.
Da Poian, G., et al., "Energy and Quality Evaluation for Compressive Sensing of Fetal Electrocardiogram Signals," Sensors 2017, vol. 17, No. 9, Dec. 22, 2016, 13 pages.
Mishra, A., et al., "ECG Signal Compression Using Compressive Sensing and Wavelet Transform," 34th Annual International Conference of the IEEE Engineering in Medicine and Biology Society, Aug. 28-Sep. 1, 2012, California, USA, 4 pages.
Polania, L. F., et al, "Compressed Sensing Based Method for ECG Compression," 2011 IEEE International Conference on Acoustics, Speech and Signal Processing (ICASSP), May 22-27, 2011, 4 pages.
Tawfic, I., et al., "Compressed Sensing of ECG Signal for Wireless System With New Fast Iterative Method," Computer Methods and Programs in Biomedicine, vol. 122, No. 3, Dec. 2015, 13 pages.
Yu, W., et al., "Adaptive compressive engine for real-time electrocardiogram monitoring under unreliable wireless channels," IET Communications, vol. 10, No. 6, Apr. 14, 2016, 9 pages.
Zhang, H., et al., "Implementation of Compressive Sensing in ECG and EEG Signal Processing," The Journal of China Universities of Posts and Telecommunications, vol. 17, No. 6, Dec. 2010, 5 pages.
Zhou, J., et al., "Asynchronous Binary Compressive Sensing for Wireless Body Sensor Networks," 2013 IEEE 9th International Conference on Mobile Ad-hoc and Sensor Networks, Dec. 11-13, 2013, 6 pages.
Advisory Action for U.S. Appl. No. 14/926,554, dated Jan. 4, 2018, 3 pages.
Non-Final Office Action for U.S. Appl. No. 14/926,554, dated Apr. 3, 2018, 12 pages.
Alonso-Atienza, Felipe et al., "Detection of Life-Threatening Arrhythmias Using Feature Selection and Support Vector Machines," IEEE Transactions on Biomedical Engineering, vol. 61, No. 3, Mar. 2014, pp. 832-840.
Amann, Anton et al., "Detecting Ventricular Fibrillation by Time-Delay Methods," IEEE Transactions on Biomedical Engineering, vol. 54, No. 1, Jan. 2007, pp. 174-177.
Andreão, Rodrigo V. et al., "ECG Signal Analysis Through Hidden Markov Models," IEEE Transactions on Biomedical Engineering, vol. 53, No. 8, Aug. 2006, pp. 1541-1549.
Author Unknown, "American Heart Association," American Heart Association, Inc., 2016, Accessed: Apr. 19, 2016, 3 pages, Available at: http://www.heart.org/HEARTORG/.
Author Unknown, "Recommendations for measurement standard in quantitative electrocardiography," European Heart Journal: The CSE Working Party, vol. 6, No. 10, Oct. 1985, pp. 815-825.
Banerjee, Swati et al., "Application of Cross Wavelet Transform for ECG Pattern Analysis and Classification," IEEE Transactions on Instrumentation and Measurement, vol. 63, No. 2, Feb. 2014, pp. 326-333.
Barro, S. et al., "Algorithmic sequential decision-making in the frequency domain for life threatening ventricular arrhythmias and imitative artefacts: a diagnostic system," Journal of Biomedical Engineering, vol. 11, No. 4, Jul. 1989, pp. 320-328.

(56) References Cited

OTHER PUBLICATIONS

Bayasi, Nourhan et al., "A 65-nm Low Power ECG Feature Extraction System," 2015 IEEE International Symposium on Circuits and Systems (ISCAS), May 2015, IEEE, pp. 746-749.

Bayasi, Nourhan et al., "Adaptive Technique for P and T Wave Delineation in Electrocardiogram Signals," 2014 36th Annual Conference of the IEEE Engineering in Medicine and Biology Society (EMBC), Aug. 26-30, 2014, Chicago, IL, pp. 90-93.

Bayasi, Nourhan et al., "Detection of Ventricular Arrhythmia Based on Unique ECG Parameters and Linear Discriminant Analysis," IEEE Transactions on Biomedical Engineering, 2014, 10 pages.

Bayasi, Nourhan et al., "Low-Power ECG-Based Processor for Predicting Ventricular Arrhythmia," IEEE Transactions on Very Large Scale Integration (VLSI) Systems, vol. 24, No. 5, May 2016, pp. 1962-1974.

Clifford, Gari D., "Chapter 3: ECG Statistics, Noise, Artifacts, and Missing Data," Advanced Methods and Tools for ECG Data Analysis, Artech House, 2006, pp. 55-99.

Coast, Douglas A. et al., "QRS Detection Based on Hidden Markov Modeling," ECG Signal Processing II, 1989, IEEE, 2 pages.

De Azevedo Botter, Eduardo et al., "A Neural Network With Asymmetric Basis Functions for Feature Extraction of ECG P Waves," IEEE Transactions on Neural Networks, vol. 12, No. 5, Sep. 2001, pp. 1252-1255.

De Chazal, Philip et al., "Automatic Classification of Heartbeats Using ECG Morphology and Heartbeat Interval Features," IEEE Transactions on Biomedical Engineering, vol. 51, No. 7, Jul. 2004, pp. 1196-1206.

Dumont J. et al.,"Parameter Optimization of a Wavelet-Based Electrocardiogram Delineator with an Evolutionary Algorithm," Computers in Cardiology, vol. 32, Sep. 2005, IEEE, pp. 707-710.

Elgendi, Mohamed et al., "Recognition of T Waves in ECG signals," 2009 IEEE 35th Annual Northeast Bioengineering Conference, Apr. 3-5, 2009, Boston, MA, 2 pages.

Fisher, R. A., "The Use of Multiple Measurements in Taxonomic Problems," Annals of Eugenics, vol. 7, No. 2, 1936, pp. 179-188.

Goldberger, Ary L. et al., "PhysioBank, PhysioToolkit, and PhysioNet: Components of a New Research Resource for Complex Physiologic Signals," Circulation, vol. 101, No. 2, Jun. 13, 2000, 7 pages.

Golpayegani, Glayol Nazari et al., "A novel approach in ECG beat recognition using adaptive neural fuzzy filter," Journal of Biomedical Science and Engineering, vol. 2, 2009, pp. 80-85.

Hamilton, Patrick S. et al., "Quantitative Investigation of QRS Detection Rules Using the MIT/BIH Arrhythmia Database," IEEE Transactions on Biomedical Engineering, vol. BME-33, No. 12, Dec. 1986, pp. 1157-1165.

Homaeinezhad, M.R. et al., "ECG arrhythmia recognition via a neuro-SVM-KNN hybrid classifier with virtual QRS image-based geometrical features," Expert Systems with Applications, vol. 39, 2012, pp. 2047-2058.

Jekova, Irena, "Shock advisory tool: Detection of life-threatening cardiac arrhythmias and shock success prediction by means of a common parameter set," Biomedical Signal Processing and Control, vol. 2, No. 1, 2007, pp. 25-33.

Khawaja, Antoun, "Automatic ECG Analysis Using Principal Component Analysis and Wavelet Transformation," Karlsruhe Transactions on Biomedical Engineering, vol. 3, Univ.-Verlag Karlsruhe, 2007, 234 pages.

Khushaba, Rami N. et al., "Driver Drowsiness Classification Using Fuzzy Wavelet-Packet-Based Feature-Extraction Algorithm," IEEE Transactions on Biomedical Engineering, vol. 58, No. 1, Jan. 2011, pp. 121-131.

Kligfield, Paul, "The Centennial of the Einthoven Electrocardiogram," Journal of Electrocardiography, vol. 35, No. 4, Part B, Oct. 2002, pp. 123-129.

Laguna, P. et al., "A Database for Evaluation of Algorithms for Measurement of QT and Other Waveform Intervals in the ECG," Computers in Cardiology, vol. 24, 1997, pp. 673-676.

Li, Cuiwei et al., "Detection of ECG Characteristic Points Using Wavelet Transforms," IEEE Transactions on Biomedical Engineering, vol. 42, No. 1, Jan. 1995, pp. 21-28.

Li, Qiao et al., "Ventricular Fibrillation and Tachycardia Classification Using a Machine Learning Approach," IEEE Transactions on Biomedical Engineering, vol. 61, No. 6, Jun. 2014, pp. 1607-1613.

Lin, Chao et al., "P- and T-Wave Delineation in ECG Signals Using a Bayesian Approach and a Partially Collapsed Gibbs Sampler," IEEE Transactions on Biomedical Engineering, vol. 57, No. 12, Dec. 2010, pp. 2840-2849.

Mallat, Stéphane, "A Wavelet Tour of Signal Processing," Academic Press, Second Edition, 1999, pp. 1-109.

Martínez, Juan Pablo et al., "A Wavelet-Based ECG Delineator: Evaluation on Standard Databases," IEEE Transactions on Biomedical Engineering, vol. 51, No. 4, Apr. 2004, pp. 570-581.

Mazomenos, E. B. et al., "A Time-Domain Morphology and Gradient based Algorithm for ECG Feature Extraction," 2012 IEEE International Conference on Industrial Technology (ICIT), Mar. 19-21, 2012, Athens, pp. 117-122.

Mazomenos, Evangelos B. et al., "A Low-Complexity ECG Feature Extraction Algorithm for Mobile Healthcare Applications," IEEE Journal of Biomedical and Health Informatics, vol. 17, No. 2, Mar. 2013, pp. 459-469.

Mehta, S. S. et al., "Detection of QRS complexes in electrocardiogram using support vector machine," Journal of Medical Engineering and Technology, vol. 32, No. 3, May/Jun. 2008, pp. 206-215.

Mehta, S. S. et al., "Recognition of P and T waves in Electrocardiograms Using Fuzzy Theory," Proceedings of the First Regional Conference IEEE Engineering in Medicine and Biology Society and 14th Conference of the Biomedical Engineering Society of India, An International Meeting, Feb. 15-18, 1995, New Delhi, pp. 2.54-2.55.

Murthy, I. S. N. et al., "Analysis of ECG from Pole-Zero Models," IEEE Transactions on Biomedical Engineering, vol. 39, No. 7, Jul. 1992, pp. 741-751.

Niknazar, Mohammad et al., "Fetal ECG Extraction by Extended State Kalman Filtering Based on Single-Channel Recordings," IEEE Transactions on Biomedical Engineering, vol. 60, No. 5, 2013, pp. 1345-1352.

Oweis, Rami J. et al., "Seizure classification in EEG signals utilizing Hilbert-Huang transform," Biomedical Engineering Online, vol. 10, No. 38, 2011, 15 pages.

Pal, Saurabh et al., "Empirical mode decomposition based ECG enhancement and QRS detection," Computers in Biology and Medicine, vol. 42, No. 1, Jan. 2012, pp. 83-92.

Pan, Jiapu et al., "A Real-Time QRS Detection Algorithm," IEEE Transactions on Biomedical Engineering, vol. BME-32, No. 3, Mar. 1985, pp. 230-236.

Pardey, J., "Detection of Ventricular Fibrillation by Sequential Hypothesis Testing of Binary Sequences," Computers in Cardiology, vol. 34, 2007, pp. 573-576.

Phyu, Myint Wai et al., "A Real-Time ECG QRS Detection ASIC Based on Wavelet Multiscale Analysis," IEEE Asian Solid-State Circuits Conference, 2009, A-SSCC 2009, Nov. 16-18, 2009, Taipei, Taiwan, pp. 293-296.

Sayadi, Omid et al., "Robust Detection of Premature Ventricular Contractions Using a Wave-Based Bayesian Framework," IEEE Transactions on Biomedical Engineering, vol. 57, No. 2, Feb. 2010, pp. 353-362.

Schleifer, J. William et al., "Ventricular Arrhythmias: State of the Art," Cardiology Clinics, vol. 31, No. 4, 2013, pp. 595-605.

Singh, Yogendra Narain et al., "ECG to Individual Identification," 2nd IEEE International Conference on Biometrics: Theory, Applications and Systems, 2008, BTAS 2008, Sep. 29-Oct. 1, 2008, Arlington, VA, 8 pages.

Sun, Yan et al., "Characteristic wave detection in ECG signal using morphological transform," BMC Cardiovascular Disorders, vol. 5, No. 28, 2005, 7 pages.

Tan, K. F. et al., "Detection of the QRS Complex, P Wave and T Wave in Electrocardiogram," First International Conference on Advances in Medical Signal and Information Processing, 2000, Bristol, pp. 41-47.

(56) References Cited

OTHER PUBLICATIONS

Tekeste, Temesghen et al., "A Biomedical SoC Architecture for Predicting Ventricular Arrhythmia," IEEE International Symposium on Circuits and Systems (ISCAS), May 22-25, 2016, Montreal, QC, IEEE, pp. 2262-2265.

Tekeste, Temesghen et al., "Adaptive ECG Interval Extraction," 2015 IEEE International Symposium on Circuits and Systems (ISCAS), May 24-27, 2015, IEEE, pp. 998-1001.

* cited by examiner

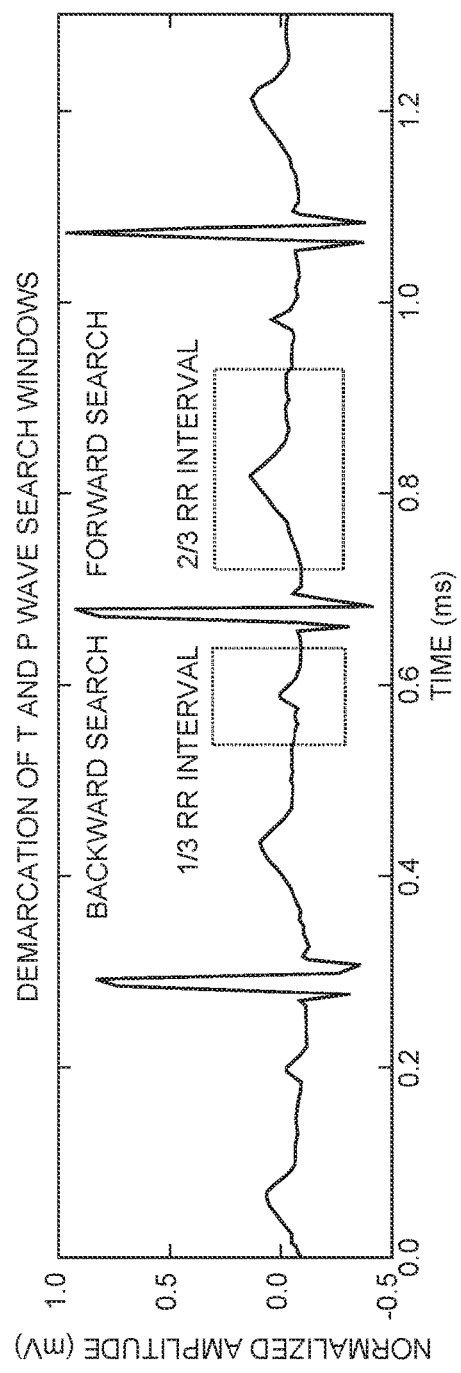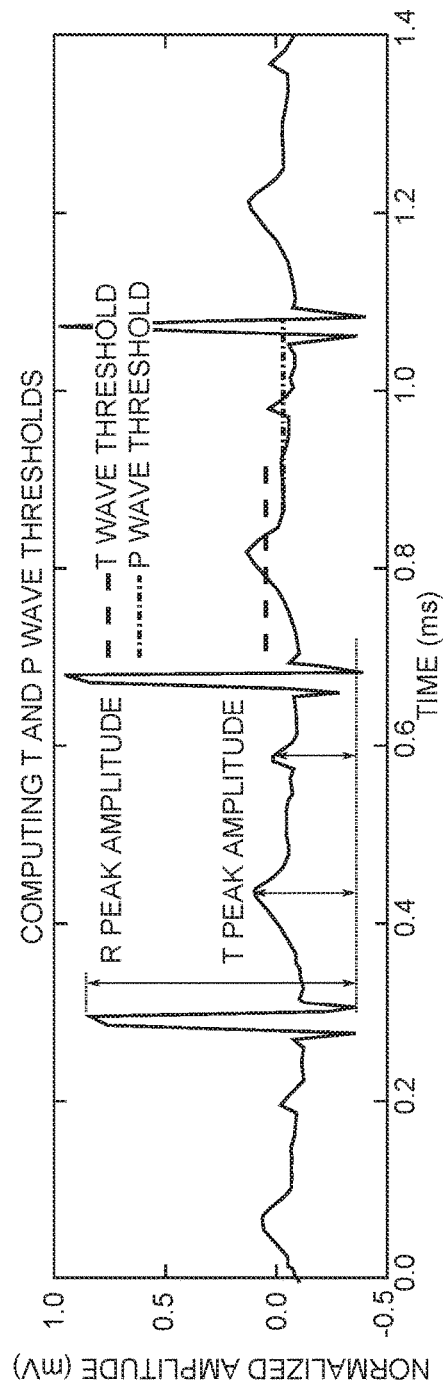

MEDICAL DEVICE AND METHOD FOR DETECTING A VENTRICULAR ARRHYTHMIA EVENT

RELATED APPLICATIONS

This application is a continuation of U.S. patent application Ser. No. 14/926,483, filed Oct. 29, 2015, now U.S. Pat. No. 9,717,438, which claims the benefit of U.S. provisional patent applications No. 62/069,975, filed Oct. 29, 2014, and No. 62/074,409, filed Nov. 3, 2014, the disclosures of which are incorporated herein by reference in their entireties.

FIELD OF THE DISCLOSURE

The present disclosure relates to biomedical devices and methods to detect arrhythmias.

BACKGROUND

Sudden cardiac death (SCD) accounts for approximately 300,000 deaths in the United States per year and in most cases is the final result of ventricular arrhythmias that include ventricular tachycardia (VT) or ventricular fibrillation (VF). Ventricular arrhythmia is a severely abnormal heart rhythm (arrhythmia) that, unless treated immediately, is responsible for 75% to 85% of sudden deaths in persons with heart problems. Most ventricular arrhythmias are caused by coronary heart disease, hypertension, or cardiomyopathy, events that result in immediate death if not accurately diagnosed or treated. VT is a fast rhythm of more than three consecutive beats originating from the ventricles at rate of more than 100 beats per minute. VF is a rhythm characterized by chaotic activity of ventricles and causes immediate cessation of blood circulation and degenerates further into a pulseless or flat electrocardiogram record indicating no cardiac electrical activity.

An implantable cardioverter-defibrillator (ICD) has been considered the best protection against sudden death from ventricular arrhythmias in high-risk individuals. However, most sudden deaths occur in individuals who do not have recognized high-risk profiles. For long-term monitoring, electrocardiography is the criterion standard for the diagnosis of ventricular arrhythmia. If the clinical situation permits, a twelve-lead electrocardiogram (ECG) is obtained and analyzed before conversion of the rhythm to detect any changes in the characteristics of the ECG signal. By extracting information about intervals, amplitude, and waveform morphologies of the different P-QRS-T waves, the onset of the ventricular arrhythmia can be detected. A wide range of algorithms and detection systems based on morphological, spectral, or mathematical parameters extracted from the ECG signal have been developed. Particular methods have shown that a combination of ECG parameters extracted from different algorithms may enhance the performance of the detection. Although these methods have exhibited advantages in the detection of ventricular arrhythmia, there are disadvantages as well. Some methods have proven quite difficult to implement or compute, while others demonstrate low specificity and low discrimination between normal and abnormal conditions. Moreover, most current methods involve a relatively late detection interval, which delays the initiation of life-saving measures.

Machine learning techniques such as neural networks and support vector machines (SVM) have been suggested as useful tools to improve the detection efficiency. However, this strategy increases the overall requirements of the detection system if not utilized or employed properly. For example, selected ECG parameters should be relevant and show significant potential in the detection of ventricular arrhythmia. Otherwise, the efficiency of a machine learning task would decrease and degrade overall performance. Thus, what is needed are a high performance yet efficient medical device and method to enable early detection of the onset of ventricular arrhythmia.

SUMMARY

A medical device and method for detecting a ventricular arrhythmia event is disclosed. The medical device includes input circuitry configured to receive an electrocardiogram (ECG) signal and processing circuitry coupled to the input circuitry that is configured to identify fiducial points within the ECG signal. Feature extraction circuitry coupled to the processing circuitry is configured to determine interval variability between the fiducial points. Machine learning circuitry is coupled to the feature extraction circuitry and is configured to detect ventricular arrhythmia based on the interval variability between the fiducial points.

Those skilled in the art will appreciate the scope of the disclosure and realize additional aspects thereof after reading the following detailed description in association with the accompanying drawings.

BRIEF DESCRIPTION OF THE DRAWINGS

The accompanying drawings incorporated in and forming a part of this specification illustrate several aspects of the disclosure and, together with the description, serve to explain the principles of the disclosure.

FIG. 2 is an ECG strip that depicts results of a formulation of T wave and P wave search windows with respect to a previously calculated RR interval.

FIG. 3 is an ECG strip chart that depicts results of computations of T wave and P wave thresholds based on previously detected T peak, P peak, and R peak values.

DETAILED DESCRIPTION

The embodiments set forth below represent the necessary information to enable those skilled in the art to practice the disclosure and illustrate the best mode of practicing the disclosure. Upon reading the following description in light of the accompanying drawings, those skilled in the art will understand the concepts of the disclosure and will recognize applications of these concepts not particularly addressed herein. It should be understood that these concepts and applications fall within the scope of the disclosure and the accompanying claims.

It will be understood that when an element such as a layer, region, or substrate is referred to as being "over," "on," "in," or extending "onto" another element, it can be directly over, directly on, directly in, or extend directly onto the other element or intervening elements may also be present. In contrast, when an element is referred to as being "directly over," "directly on," "directly in," or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

Section 1. Introduction

The present disclosure provides a high-performance yet efficient method for early detection of the onset of ventricular arrhythmia by combining six electrocardiogram (ECG) parameters. The six ECG parameters include PQ interval variability, QP interval variability, RT interval variability, TR interval variability, PS interval variability, and SP interval variability. No combination of these parameters has previously been used for detecting ventricular arrhythmia. However, the present disclosure demonstrates that the above six parameters are the most significant set of parameters for the detection of ventricular tachycardia and ventricular fibrillation (VT/VF) events.

Figure 1:
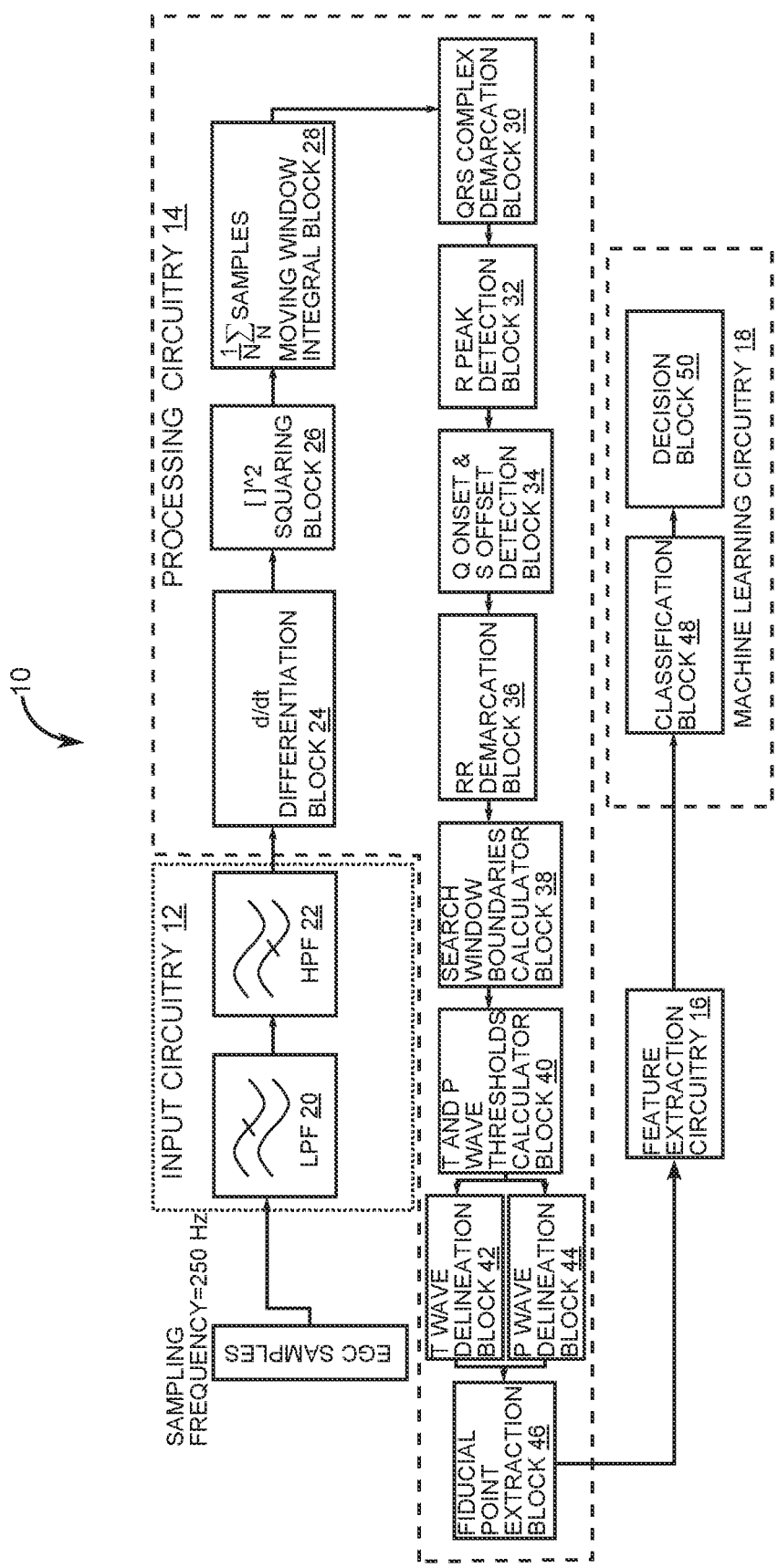
FIG. 1 is a schematic diagram depicting a medical device for detecting a ventricular arrhythmia event of the present disclosure.

FIG. 1 is a schematic diagram depicting a medical device 10 of the present disclosure for detecting a ventricular arrhythmia event. In particular, the medical device 10 is a fully integrated ECG signal processing system suitable for real-time and efficient applications requiring detection of a ventricular arrhythmia event. Medical device 10 comprises input circuitry 12 that is configured to receive an ECG signal. Processing circuitry 14 is coupled to the input circuitry 12 and is configured to identify at least one fiducial point of a first heartbeat signature and the at least one fiducial point of a second heartbeat signature, wherein each of the at least one fiducial point is associated with at least one of the six ECG parameters. However, it is to be understood that the each of the at least one fiducial point is not limited to just the six ECG parameters listed above. Other ECG parameters such as upper and lower envelope variations are also usable.

Feature extraction circuitry 16 is coupled to the processing circuitry 14 and is configured to determine at least one difference between the at least one first fiducial point of the first heartbeat signal and the at least one first fiducial point of the second heartbeat signal. Machine learning circuitry 18 is coupled to the feature extraction circuitry 16 and is configured to select a ventricular arrhythmia class based on the at least one difference.

In more detail, the input circuitry 12 includes a low-pass filter 20 and a high-pass filter 22 that are configured to remove unwanted noise signals coupled within the ECG signal. Once filtered, the ECG signal is received by the processing circuitry 14, which includes a differentiation block 24 that takes a derivative of the filtered ECG signal. A squaring block 26 is configured to square the derivative of the filtered ECG signal before a moving window integral block 28 integrates data samples within the ECG signal that contains at least two QRS complexes, two P waves, and two T waves from at least two heartbeat signatures. A QRS complex demarcation block 30 is configured to locate the two or more QRS complexes. An R peak detection block 32 is configured to locate the R peaks within the QRS complexes once the QRS complex demarcation block 30 provides demarcation of the QRS complexes. A Q onset and S offset detection block 34 is configured to search and detect Q onsets and S offsets for each of the QRS complexes demarcated.

An RR demarcation block 36 is configured to determine the interval between two R peaks detected by the R peak detection block 32. Typically, the two R peaks are automatically selected from two consecutive heartbeat signatures. A search window boundaries calculator block 38 is configured to perform calculations to determine search window boundaries that will contain T wave and P wave fiducial points. The calculations performed take into consideration the sampling frequency of the ECG signal. For instance, the search window boundaries may select more sample points for a higher frequency ECG sampling. While FIG. 1 depicts the ECG sampling frequency as being 250 Hz, other sampling frequencies such as 360 Hz are usable with the search window boundaries calculator block 38.

A T and P wave thresholds calculator block 40 is configured to calculate amplitude thresholds for the T waves and the P waves within the window boundaries calculated by the search window boundaries calculator block 38. A T wave delineation block 42 is configured to determine a precise location for each of the T waves using T wave amplitude thresholds received from the T and P wave thresholds calculator block 40. Similarly, a P wave delineation block 44 is configured to determine a precise location for each of the P waves using P wave amplitude thresholds received from the T and P wave thresholds calculator block 40.

A fiducial point extraction block 46 is configured to find fiducial points within the calculated search window boundaries. The fiducial points extracted can be but are not limited to P peak, P offset, Q onset, R peak, S offset, T peak and T offset. Medical device 10 along with the following disclosed techniques takes into account different ECG waveform morphologies and utilizes adaptive search windows along with thresholds to accurately detect the fiducial points of each heartbeat.

In an exemplary embodiment, the feature extraction circuitry 16 is configured to extract six parameters from search windows placed within the ECG signal. In this exemplary embodiment, the search window size is around five seconds of an ECG signal. Once features are extracted, various other unique combinations of the parameters are constructed and used as input for the machine learning circuitry 18, which includes a classification block 48 that is configured to classify the extracted features and a decision block 50 that is configured to determine if a ventricular arrhythmia event is occurring based upon the classification of the extracted features.

In this regard, linear discriminant analysis (LDA) has been employed by the machine learning circuitry 18 to distinguish healthy individuals from individuals susceptible to ventricular arrhythmia. The use of LDA by the machine learning circuitry introduces a strong potential for detection of ventricular arrhythmia with a P value less than 0.001 when using ECG parameters. Secondly, a strong biasing effect of the classification block 48 is avoided when using ECG parameters combined with the LDA. Thirdly, LDA is the simplest classification algorithm that can be employed using ECG parameters.

Five combinations of the six ECG parameters were evaluated by different K-fold cross validations, which include fivefold, sevenfold, and tenfold cross validations. The five combinations were constructed based upon an output rank of information gained feature selection technique. A best performance was found to be a combination that included all the extracted parameters using tenfold cross validation. Yet, the performance of the other combinations also revealed good results.

Remaining portions of this disclosure are organized as follows. In section II, ECG detection and delineation techniques are highlighted. Section III represents a feature construction stage along with analysis of building different combinations of the six ECG parameters. A classification algorithm implemented by classification block 48 is described in section IV. Performance and results as well as a comparison with other detection methods are reported in section V.

Section 2. ECG Signal Processing

In order to detect the QRS complex, the Pan and Thompkins (PAT) algorithm is used. PAT is a commonly used algorithm based upon an amplitude threshold detection technique that exploits the fact that R peaks have higher amplitudes compared to other ECG wave peaks. With proper pre-filtering of an ECG signal, the PAT algorithm is highly efficient at detecting the R peaks in every heartbeat signature using an upper threshold level and lower threshold level.

A novel implementation of a delineation algorithm for the T and P waves is provided in this disclosure. The delineation algorithm is based on adaptive search windows along with adaptive threshold levels to accurately distinguish T and P peaks from noise peaks. In each heartbeat, the QRS complex is used as a reference for the detection of T and P waves in which two regions are demarcated with respect to an interval between QRS complexes and is commonly referred to as the RR interval. These regions are then used to form forward and backward search windows of the T and P waves respectively, as shown in FIG. 2. A forward search window is assumed to contain the T wave and the boundaries are extended from the QRS offset to two thirds of the RR interval.

Positions of T and P peaks are registered by finding either a local maximum or and a local minimum in each of the search windows and then comparing them to the associated thresholds. A threshold for a T wave is given in equation 1, while a threshold for a P wave is given in equation 2.

$$T_{wave_{th}} = \frac{T_{peak}}{R_{peak}} t_{thresh_{in}} \quad (1)$$

$$P_{wave_{th}} = \frac{P_{peak}}{R_{peak}} p_{thresh_{in}} \quad (2)$$

Each threshold given in equation 1 and equation 2 is modified in each heartbeat signature based on the most recent detected values during a predetermined time period, such as five seconds. Scaling factors $t_{thresh_{in}}$ and $p_{thresh_{in}}$ are each set within a range of 0.1 to 0.2 based on the most recent detected values in the last processing window. A technique for computing the thresholds is shown in FIG. 3. By comparing the local maximum and/or the local minimum points with the thresholds, the waveform morphology of each wave is identified. For example, the waveform morphology can be, but is not limited to, positive monophasic, negative monophasic, or biphasic morphologies.

The delineation algorithm traces onset and offset values of the P-QRS-T waves by finding a sample corresponding to a zero slope of a sampled ECG signal. A sample point that has a zero slope and is located before the peak is identified as the onset point. Similarly, the offset point is determined at the later side of the peak. At times, however, a derivative sign change occurs, which causes a false indicator. To solve this problem, the delineation algorithm adds additional criteria for a correct delineation of the wave boundaries based upon fiducial points that tend to merge smoothly with an isoelectric line. The isoelectric line is approximated as the average value of the heartbeat signature after removing the QRS complex. The fact that the fiducial points tend to merge smoothly with the isoelectric line is used in combination with location of the zero slope point to accurately and reliably delineate the fiducial points.

Section 3. Feature Construction

Feature construction begins when the machine learning circuitry 18 compiles data from the ECG raw data signals. A selection of ECG parameters for a machine learning algorithm as implemented by the machine learning circuitry 18 of the present disclosure is an important consideration as selection of ECG parameters determines cost, running time, and overall performance of the medical device 10 that executes the machine learning algorithm by way of the machine learning circuitry 18. Once the machine learning circuitry 18 compiles data from the ECG raw data signals, advanced ECG parameter extraction from the ECG raw data signals can begin. In an exemplary embodiment the ECG data is analyzed and processed in a time window of five seconds to extract a set of six parameters representing two consecutive cardiac states in every window. Moreover, the extracted parameters are normalized to the average maximal QRS deviation over an entire ECG recording and corrected with respect to the RR interval to provide an accurate analysis regardless of the gender or age of the patient whose ECG is recorded. In an exemplary embodiment, the extracted parameters are mathematically independent of each other.

In at least one embodiment, at least 50 parameters have been extracted from an ECG signal based upon morphological, spectral, and mathematical analysis of the ECG signal. Exemplary ones of the 50 parameters are listed in Table I below.

TABLE I

EGC Parameters Used With The Exemplary Embodiments

| Morphological Parameter | Spectral Parameter | Mathematical Parameter |
| --- | --- | --- |
| Intervals | Discrete Cosine Transform | Hankel Transform |
| Segments | Discrete Fourier Transform | Abel Transform |
| Amplitudes | Laplace Transform | |
| Areas | | |
| Area Asymmetry | | |
| Interval Asymmetry | | |
| Upper Envelope Variation | | |
| Lower Envelope Variation | | |

Some of the ECG parameters listed in Table I have been previously defined in other works and others are new in the detection field. To choose ECG parameters having a maximum discrimination characteristic for detecting a ventricular arrhythmia event, statistical analysis of mean error and standard deviation two-sided unpaired t-test and feature selection by filtering have been performed individually. In particular, the statistical analysis was used to assess separation between normal and abnormal ECG records. In the two-sided unpaired t-test, a P value less than 0.001 in the 95% confidence interval (CI) has been considered as statistically significant. Similarly, an area under a receiver operating characteristics (ROC) curve, area under the curve (AUC) is selected to be greater than 95% for further analysis. From this further analysis, an ECG parameter in the feature selection analysis has been selected to provide the highest arrhythmia detection accuracy generated from a single ECG parameter. This ECG parameter is combinable with other individual ECG parameters of high relevance to provide preferred combinations of the six ECG parameters for even greater arrhythmia detection accuracy.

Section 3.1. ECG Databases

A study conducted in verification of the embodiments of the present disclosure included two groups, GROUP A and GROUP B. GROUP A included ECG records for persons having normal ECGs, while GROUP B included persons susceptible to ventricular arrhythmia. GROUP A included a set of 18 single-lead normal ECG records obtained from the Massachusetts Institute of Technology-Beth Israel Hospital (MIT/BIH) normal sinus rhythm database (NSRDB). The GROUP A ECG records were sampled at 250 Hz and had no significant arrhythmias. In contrast, GROUP B included 20 single-lead abnormal ECG records with significant ventricular arrhythmias. The GROUP B abnormal ECG records were obtained from different sources including American Heart Association (AHA) Database records sampled at 250 Hz, MIT-BIH ECG records sampled at 360 Hz, and Creighton University Database (CUDA) records sampled at 250 Hz. Table II below provides additional details that match a particular database with particular cardiac anomalies.

TABLE II

EGC Records from Different Databases

| Database | Quantity | Length | Arrhythmia Categories |
| --- | --- | --- | --- |
| NSRDB | 18 Records | 24-Hours | Not Applicable |
| AHA | 10 Records | 3-Hours | Ventricular Tachycardia, Ventricular Flutter, Ventricular Fibrillation |
| MIT-BIH | 5 Records | 30-Minutes | Ventricular Tachycardia, Ventricular Flutter |
| CUDA | 5 Records | 8-Minutes | Ventricular Tachycardia, Ventricular Flutter, Ventricular Fibrillation |

Section 3.2 Short-Term ECG Parameters

A learning algorithm is strongly affected by the number and relevance of input variables. As such, analyses performed for this disclosure studied the ECG parameters listed in Table I. Each ECG parameter was examined independently with various discrimination techniques to determine the most analytically useful parameters. A unique set of six morphological ECG parameters was found to be the most indicative characteristics of ventricular arrhythmia episodes. The set of six morphological ECG parameters includes PQ interval variability, QP interval variability, RT interval variability, TR interval variability, PS interval variability, and SP interval variability.

Figure 4:
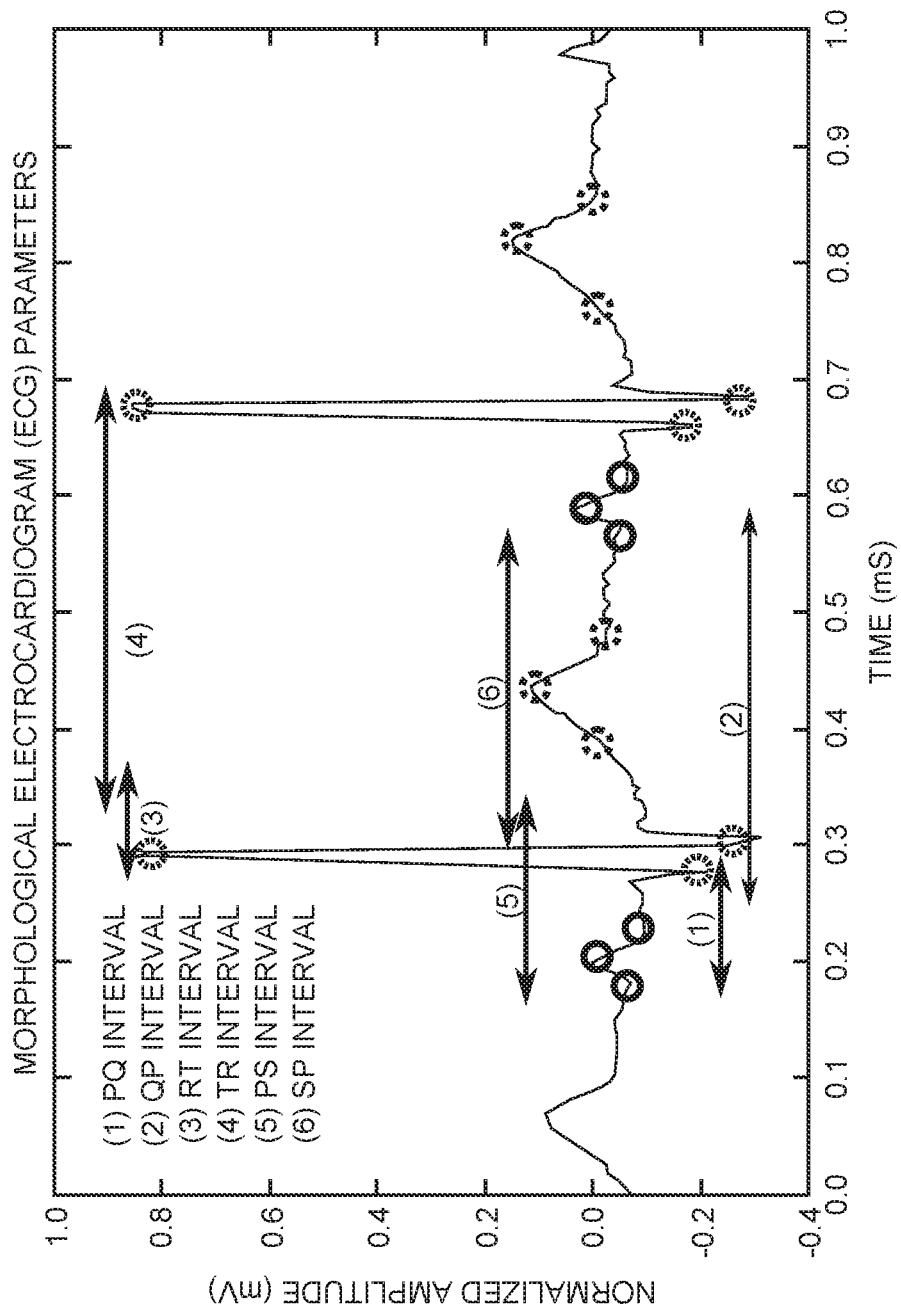
FIG. 4 is an ECG strip chart that shows six ECG parameters that are usable with techniques of the present disclosure.

FIG. 4 is an exemplary ECG graphic depicting the set of six morphological ECG parameters. The PQ interval represents the interval from the atrial depolarization to the ventricular depolarization and is measured from the beginning of the P wave to the onset of the QRS complex, while the QP interval is measured from the onset of the QRS complex to the beginning of the P wave of the next cardiac cycle. The RT interval is the duration of the ventricular systole in which the ventricles remain in a depolarized state. The RT interval is measured from the peak of the R wave to the start of the T wave. In contrast, the TR interval defines the ventricular diastole interval, which provides a determination of how long the ventricles refill with blood following contraction.

The TR interval is measured from the start of the T wave of one cardiac cycle to the peak of the R wave of the next cardiac cycle. The time interval between the start of the P wave and the end of the S wave and between the end of the S wave of one cycle and the beginning of the P wave of the next cycle define PS interval and SP interval, respectively.

Figure 5:
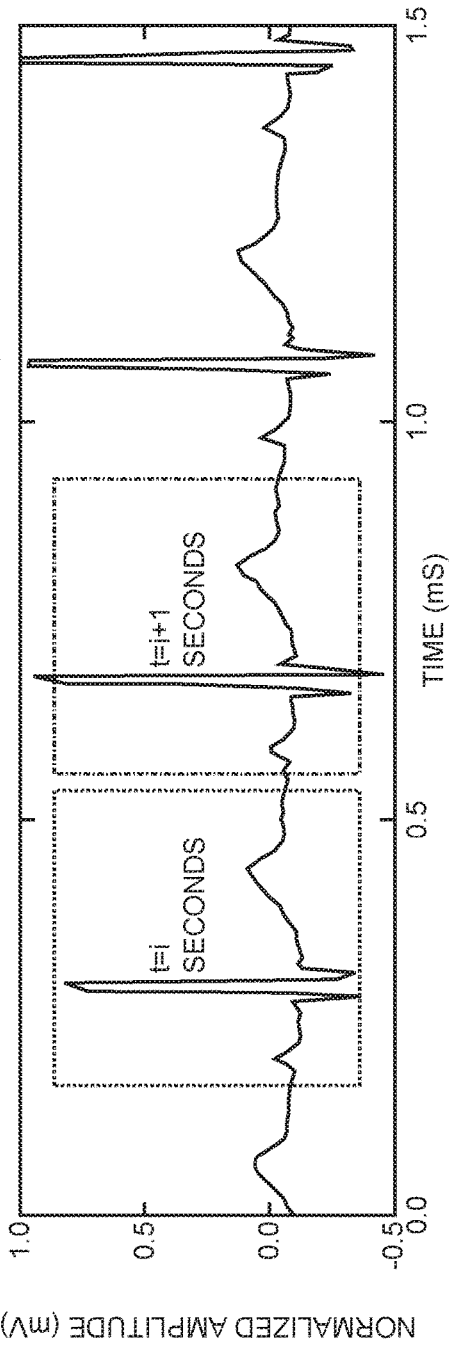
FIG. 5 is an ECG strip chart diagram of a related-art ECG processing technique that uses processing windows that each contain only one heartbeat signature.
Figure 6:
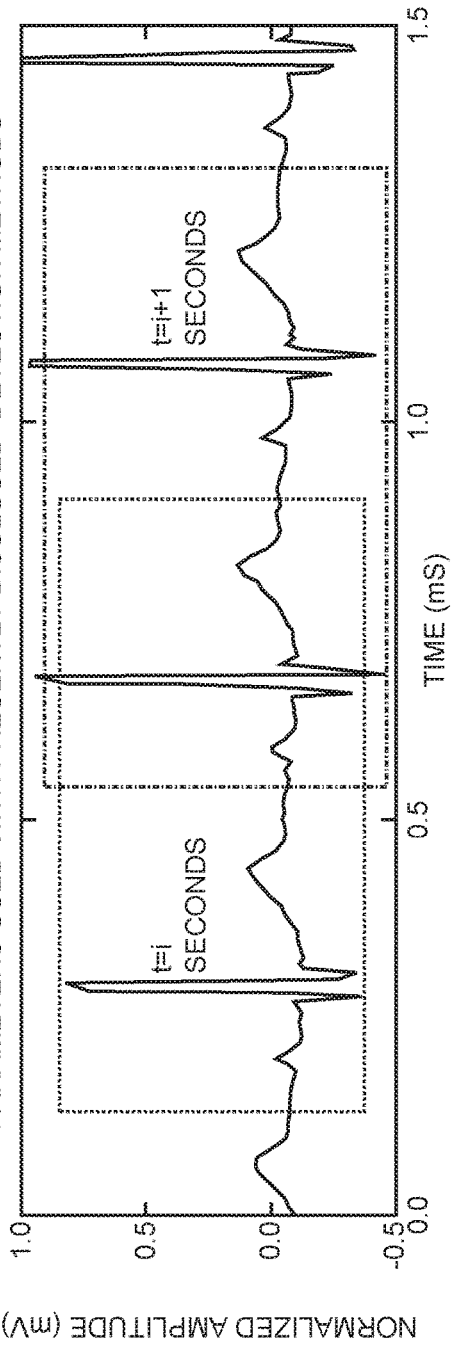
FIG. 6 is an ECG strip chart diagram of an ECG processing technique using processing windows that each contain two heartbeat signatures in accordance with the present disclosure.
Figure 7A:
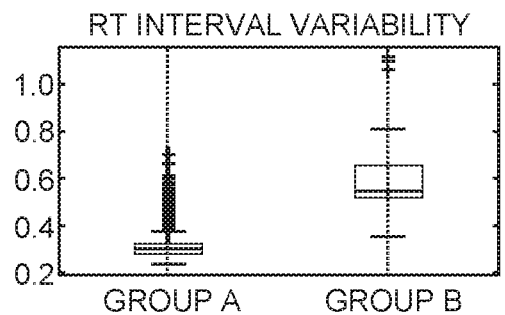
FIG. 7A is a box and whisker diagram depicting RT interval variability between GROUP A normal ECG samples and GROUP B abnormal ECG samples.
Figure 7B:
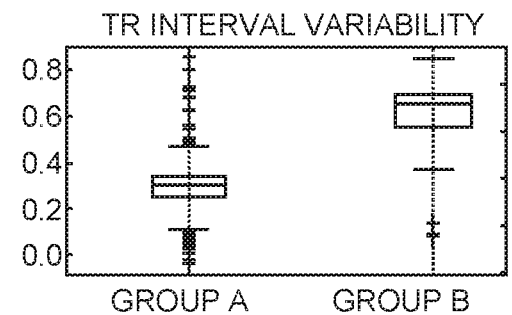
FIG. 7B is a box and whisker diagram depicting TR interval variability between GROUP A normal ECG samples and GROUP B abnormal ECG samples.
Figure 7C:
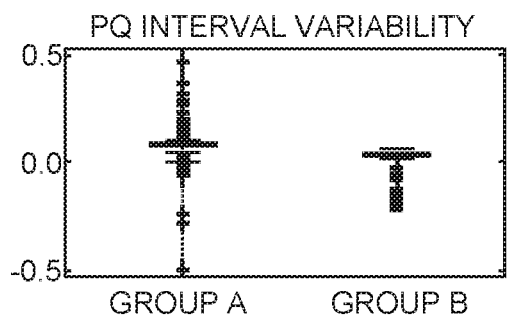
FIG. 7C is a box and whisker diagram depicting PQ interval variability between GROUP A normal ECG samples and GROUP B abnormal ECG samples.
Figure 7D:
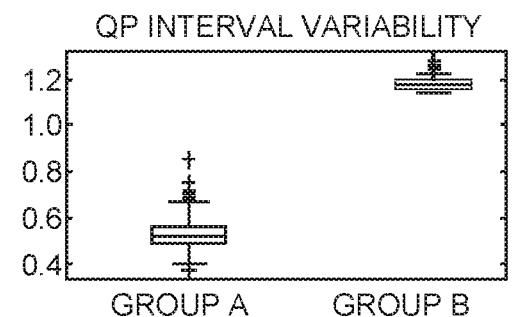
FIG. 7D is a box and whisker diagram depicting QP interval variability between GROUP A normal ECG samples and GROUP B abnormal ECG samples.
Figure 7E:
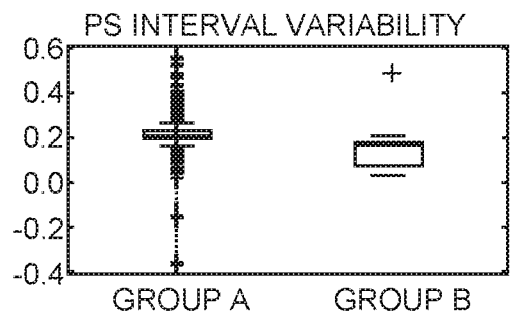
FIG. 7E is a box and whisker diagram depicting PS interval variability between GROUP A normal ECG samples and GROUP B abnormal ECG samples.
Figure 7F:
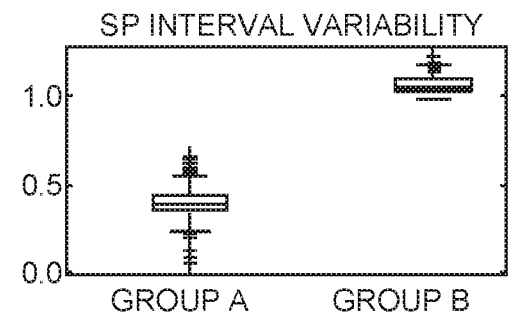
FIG. 7F is a box and whisker diagram depicting SP interval variability between GROUP A normal ECG samples and GROUP B abnormal ECG samples.

FIG. 5 is an ECG strip chart diagram of a related-art ECG processing technique that uses processing windows that each contain only one heartbeat signature. Unlike other detection algorithms, which depend on the common ECG parameters extracted from a single cardiac cycle as shown in FIG. 5, embodiments of the present disclosure process every two consecutive cycles together and relate pattern changes in the extracted ECG parameters to ventricular arrhythmia as depicted in FIG. 6.

Section 3.3. Statistical Analysis

FIGS. 7A through 7F are box and whisker plots of the set of six ECG parameters comparing GROUP A with GROUP B. Table III below provides tabulated data for the box and whisker plots depicted in FIGS. 7A through 7F.

TABLE III

Statistical Analysis of the Set of Six EGC Parameters

| Parameter | μ ± σ GROUP A | μ ± σ GROUP B | p-value |
|---|---|---|---|
| PQ Interval Variability | 0.073 ± 0.0538 | 0.0222 ± 0.0395 | <0.001 |
| QP Interval Variability | 0.5311 ± 0.0532 | 1.18 ± 0.003 | <0.001 |
| RT Interval Variability | 0.322 ± 0.0067 | 0.607 ± 1723 | <0.001 |
| TR Interval Variability | 0.283 ± 0.095 | 0.598 ± 1742 | <0.001 |
| PS Interval Variability | 0.21 ± 0.057 | 0.144 ± 0.071 | <0.001 |
| SP Interval Variability | 0.396 ± 0.062 | 1.065 ± 0.0598 | <0.001 |

The statistics listed in Table III illustrate discernable delineations between the set of six ECG parameters for each of GROUP A and GROUP B for a p<0.001. For example, the mean value of the PQ interval variability is slightly greater for GROUP A and GROUP B, and a similar observation is made for the PS interval variability. However, the QP interval variability, the RT interval variability, the TR interval variability, and the SP interval variability have significantly higher delineations between the set of six ECG parameters for GROUP A and GROUP B for a p<0.001. In particular, the mean error in GROUP B is at least twice the mean error of GROUP A.

Section 3.4. Information Gain Attribute Evaluation

Filter-based feature selection (FS) was used to prioritize delineation efficiency of the six ECG parameters. Filter-based FS is independent of the machine learning classifier of the machine learning circuitry 18 (FIG. 1) and uses an attribute evaluator and a ranker to rank all the parameters in the original data set. In this disclosure, an information gain (IG) attribute evaluator was applied.

Entropy, which measures a system's unpredictability, is used as the foundation for the IG attribute evaluator. The entropy of Y, H(Y), is given in equation 3.

$$H(Y) = -\sum_{y \in Y} p(y) \log_2(p(y)) \quad (3)$$

where p(y) is the marginal probability density function for the random variable Y In some cases the observed values of Y in the training data set are partitioned according to the values of the second feature X In this case, the entropy of Y after observing X is given in equation 4.

$$H(Y|X) = -\sum_{x \in X} p(x) \sum_{y \in Y} p(y|x) \log_2(p(y|x)) \quad (4)$$

where p(y|x) is the conditional probability of y given x. The IG measurement reflects information about Y provided by X and is given by equation 5.

$$IG = H(Y) - H(Y|X) \quad (5)$$

In this disclosure, Y is the class (GROUP A and GROUP B) and X is the vector containing the six ECG parameters.

Section 4. Classification Model

Embodiments of this disclosure use linear discriminant analysis (LDA), a technique developed by R. A. Fisher in 1936 to discriminate ventricular arrhythmia versus non-ventricular arrhythmia. In particular, the parameters PQ interval variability, QP interval variability, PS interval variability, SP interval variability, RT interval variability, and TR interval variability are extracted from ECG signals to produce a new data set that is processed using LDA to discriminate ventricular arrhythmia versus non-ventricular arrhythmia. LDA is executed in the classification block 48 (FIG. 1) of the machine learning circuitry 18.

LDA is mathematically robust and produces models with accuracy equivalent to more complex delineation methods when input variables have a strong correlation with the monitored ECG signal. As such, embodiments of the present disclosure use LDA to perform classification.

In an exemplary embodiment, a projection of samples x onto a line y is given by equation 6.

$$y = w^T x \quad (6)$$

The goal of implementing LDA is to provide a relatively large separation between the class means, while also keeping the in-class variance relatively small. A mathematical formulation of this goal is realized by maximizing the Fisher criterion J(w), which is given in equation 7.

$$J(w) = \frac{|\tilde{\mu}_1 - \tilde{\mu}_2|}{\tilde{s}_1^2 + \tilde{s}_2^2} \quad (7)$$

$\tilde{\mu}$ is the main vector of each class in the y feature space, given in equation 8.

$$\tilde{\mu} = \frac{1}{N_i} \sum_{y \in w_i} y = \frac{1}{N_i} \sum_{x \in w_i} w^T x \quad (8)$$

$\tilde{s}^2$ is the variance, given in equation 9.

$$\tilde{s}^2 = \sum_{y \in \omega_i} (y - \tilde{\mu}_i^2) \quad (9)$$

The final Fisher criterion J(w), can be rewritten by defining the between-class variable ($S_B$) and the within-class variable ($S_W$) given in equations 10 and 11, respectively.

$$S_B = (\mu_1 - \mu_2)(\mu_1 - \mu_2)^T \quad (10)$$

$$S_W = \sum_{i=1,2} \sum_{n=1}^{N_i} (x_n^i - \mu_i)(x_n^i - \mu_i)^T \quad (11)$$

Thus, the final Fisher Criterion J(w), can be re-written as given in equation 12.

$$J(w) = \frac{w^T S_B w}{w^T S_W w} \quad (12)$$

By differentiating J(w), with respect to w, and setting the result to zero, a generalized eigenvalue problem yields equation 13, which specifies a choice of direction for a projection of data down to 1-d.

$$w = S_W^{-1}(\mu_1 - \mu_2) \quad (13)$$

An analysis of the classification procedure randomly divided each parameter data set into different training, testing, and validation data sets to determine maximum classification performance. During training and testing, 64% of the parameter data was used for training the classifier, whereas the remaining 36% was split equally into a testing data set and a validation data set. A training and testing procedure was then repeated several times to ensure that results were independent of introduced randomization.

Various combinations of the selected training parameters were fed into the LDA model as input and then the models were evaluated on the corresponding combination test data. Each combination was validated using ten K-fold cross validations on the parameter data set. An average of the K fold cross validations was ultimately used for evaluation.

Section 5. Performance and Results

Section 5.1. ECG Signal Detection and Delineation

The performance of the implemented QRS complex demarcation block 30 (FIG. 1) was assessed by evaluating the sensitivity (SE) and precision (P) as shown in equations 14 and 15.

$$SE = \frac{TP}{TP + FN} \quad (14)$$

$$P = \frac{TP}{TP + FP} \quad (15)$$

where TP is a variable representing true detections, FN is a variable representing false negative detections, and FP is a variable representing false positive detections. During testing, the QRS complex demarcation block 30 achieved a sensitivity SE=99.8% and a precision of P=98.6%.

Moreover, the mean error ($\mu$) and the standard deviation ($\sigma$) of the fiducial points including the P peak, the P offset, the Q onset, the R peak, the S offset, the T peak, and T offset were calculated between the annotated and automated results, which are listed Table IV below.

TABLE IV

PERFORMANCE EVALUATION OF THE ECG SIGNAL PROCESSING ALGORITHM

| Parameter | $P_{peak}$ | $P_{off}$ | $Q_{on}$ | $R_{peak}$ | $S_{off}$ | $T_{peak}$ | $T_{off}$ |
|---|---|---|---|---|---|---|---|
| $\mu$ (ms) | 5.5050 | −2.5962 | −4.9719 | −1.1025 | −4.9719 | −1.3671 | 6.3682 |
| $\sigma$ (ms) | 8.6467 | 7.9140 | 6.7037 | 4.5076 | 6.7037 | 12.0788 | 14.6465 |

Figure 8:
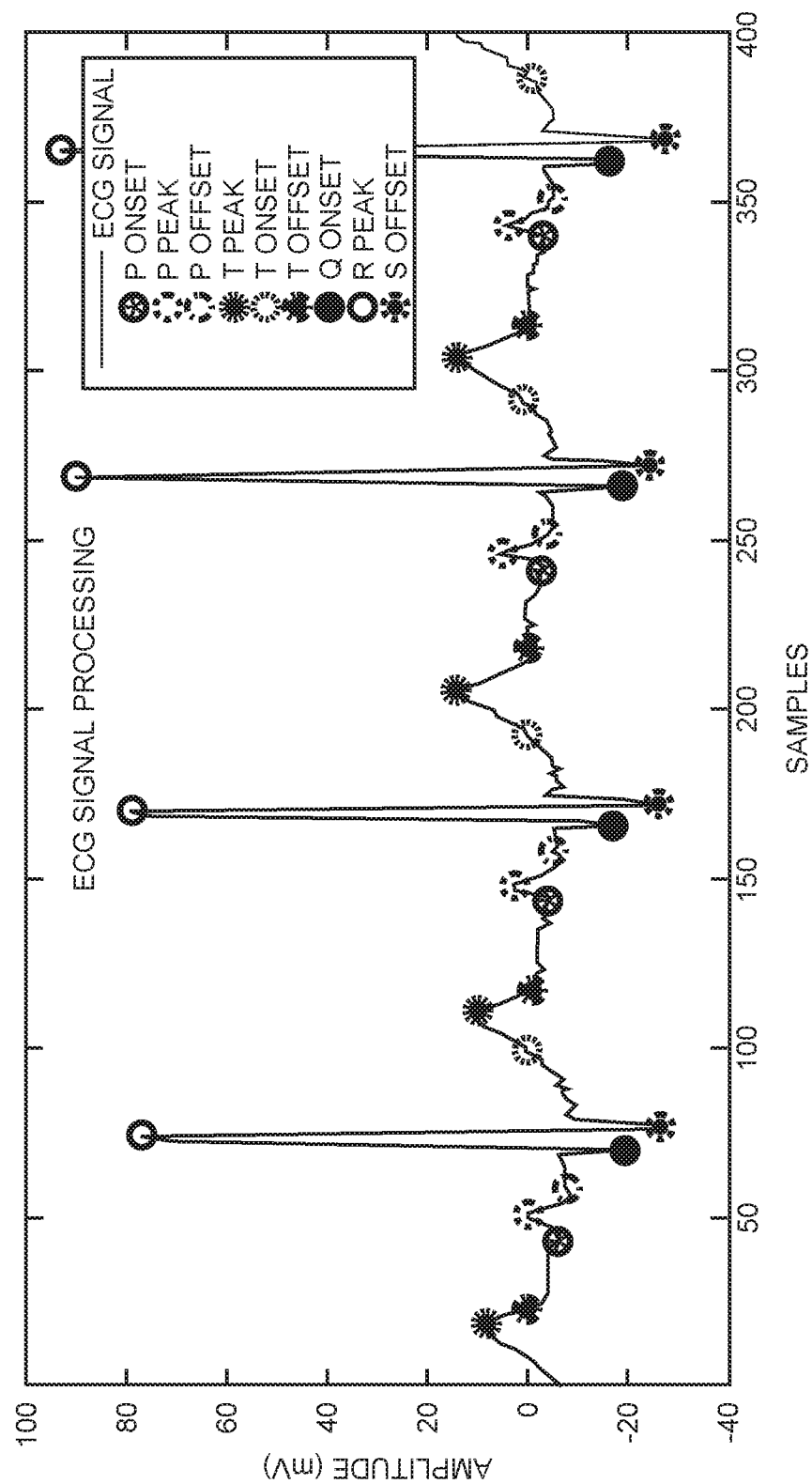
FIG. 8 is an ECG strip chart illustrating QRS complex detection and T wave and P Wave delineation.

FIG. 8 is an annotated ECG chart that is representative of the results of QRS complex detection along with T wave and P wave delineation using the embodiments of the present disclosure. FIG. 8 illustrates that the detection and delineation algorithm has accurately identified all of the fiducial points within a preselected search window that captures every heartbeat signature.

Section 5.2. Performance of Individual Parameters

Table V shows the rank of the six EGC parameter sorted by the IG feature selection. The ranking was used to form the different combinations of the ECG parameters. The performances of the individual ECG parameters based on the LDA, and using training and test data set with a five second sampling window length, is presented in Table VI. Accuracy (ACC) is calculated using equation 16.

$$ACC = \frac{TP + TN}{TP + TN + FP + FN} \quad (16)$$

Figure 9:
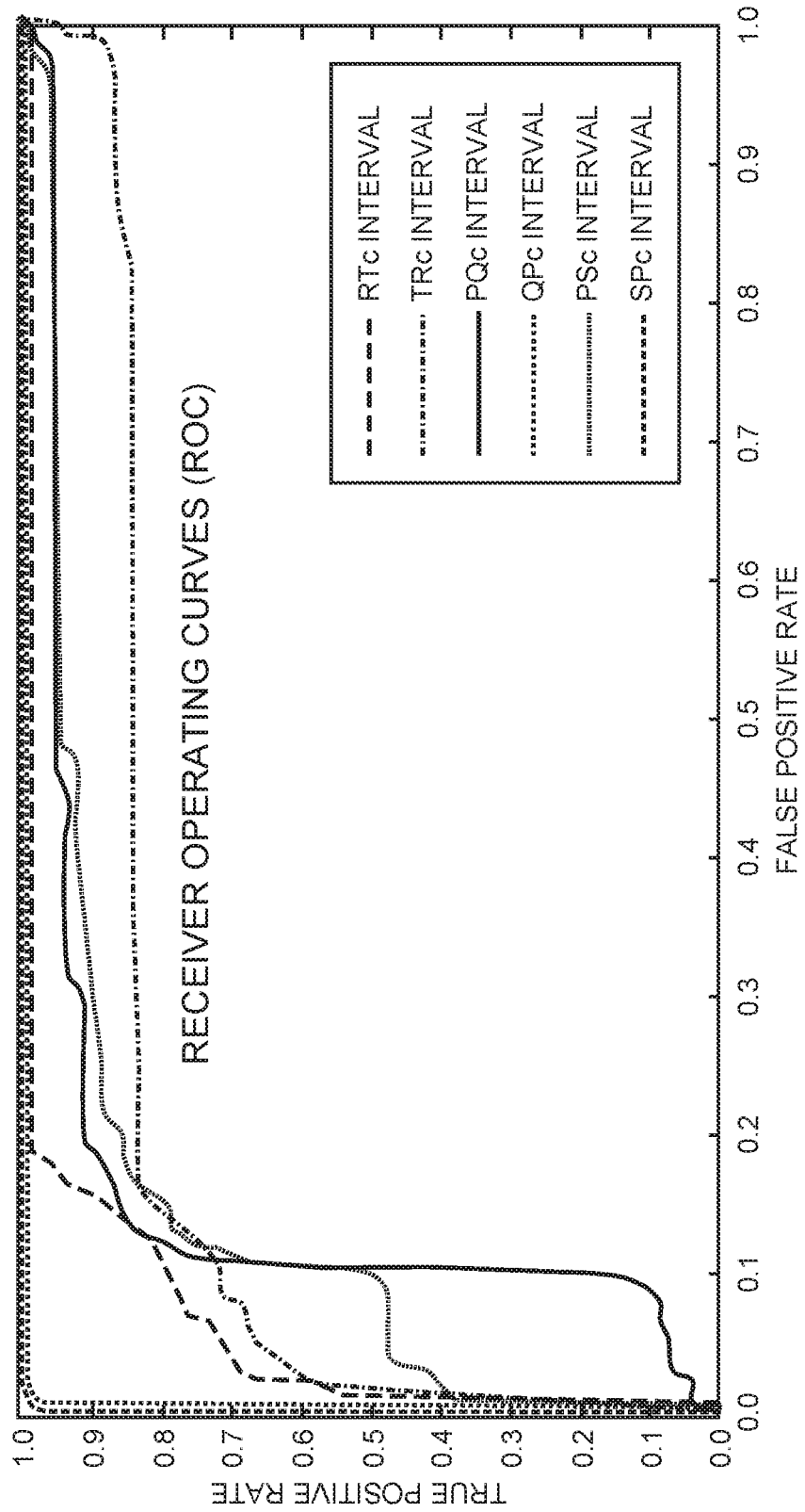
FIG. 9 is a graph depicting receiver operating characteristics curves calculated for ventricular arrhythmia versus non-ventricular arrhythmia conditions.

The individual discrimination ability of each ECG parameter was studied by analyzing ROC curves shown in FIG. 9. The performance of the parameters was assessed by determining the area under the ROC curves as shown in FIG. 9. All of the parameters provided good performance having an AUC greater than 99%. Table V below lists the ranking of each of the six ECG parameters. A ranking analysis of the ECG parameters was conducted using filter-based feature selection.

TABLE V

RANKING ANALYSIS OF ECG PARAMETERS USING FS BY FILTER

| Rank | Parameter |
|---|---|
| 1 | QP interval variability |
| 2 | SP interval variability |
| 3 | RT interval variability |
| 4 | TR interval variabiliiy |
| 5 | PQ interval variability |
| 6 | PS interval variability |

Section 5.3. Performance of Parameter Combinations

Different unique combinations of the ECG parameters were tested to find out the set with the maximum accuracy.

A first combination contained the top two ranked parameters including the QP interval variability and the SP interval variability. Next, for each new combination, a new parameter was added until a final combination included all six ECG parameters. Please see Table VI.

TABLE VI

PERFORMANCE OF THE INDIVIDUAL PARAMETERS USED IN THIS WORK (WINDOW SIZE = 5 SEC)

| Parameter | Training set (%) | | | | Testing set (%) | | | |
|---|---|---|---|---|---|---|---|---|
|  | ACC | SE | P | AUC | ACC | SE | P | AUC |
| QP int. var. | 99.4 | 99.3 | 99.4 | 99.82 | 99.1 | 96 | 99.8 | 99.3 |
| SP int. var. | 99.66 | 99.7 | 97.8 | 99.7 | 99.3 | 95.4 | 99.5 | 99.5 |
| RT int. var. | 98.84 | 97.5 | 97.8 | 99.5 | 98.26 | 95.3 | 99.6 | 99.64 |
| TR int. var. | 97.16 | 97.2 | 97.7 | 99.8 | 97.1 | 93.1 | 98.9 | 99.06 |
| PQ int. var. | 96.78 | 96.8 | 96 | 99.09 | 96.9 | 93.9 | 98.8 | 99.01 |
| PS int. var. | 96.24 | 95.5 | 95.22 | 99.004 | 96.4 | 95.5 | 98.9 | 99.01 | int. = interval
var. = variability

Table VII lists the performance of the ECG parameter combinations using a five-second window length. Note that the maximum accuracy obtained by training and testing was the fifth combination. As such, combining information from all six ECG parameters provides the most robust detection system for cardiac arrhythmia and/or other cardiac failure signals.

TABLE VII

PERFORMANCE OF THE PARAMETER COMBINATIONS USED IN THIS WORK (WINDOW SIZE = 5 SEC)

| Combination number | Combination parameter | Training set (%) | | | | Testing set (%) | | | |
|---|---|---|---|---|---|---|---|---|---|
|  |  | ACC | SE | P | AUC | ACC | SE | P | AUC |
| #1 | QP, SP interval variability | 98.89 | 98.1 | 96.2 | 99.81 | 98.95 | 96.1 | 99.36 | 99.88 |
| #2 | QP, SP, RT interval variability | 99.01 | 99.2 | 98.4 | 99.909 | 99.071 | 96.4 | 99.2 | 99.901 |
| #3 | QP, SP, RT, TR interval variability | 97.21 | 98.3 | 95.2 | 99.7 | 97.1 | 95.2 | 98.3 | 99.67 |
| #4 | QP, SP, RT, TR, PQ interval variability | 99.13 | 97.1 | 98.24 | 99.9 | 99.3 | 98.9 | 99.44 | 99.05 |
| #5 | QP, SP, RT, TR, PQ, PS interval variability | 98.98 | 98.9 | 98.99 | 99.96 | 99.1 | 97.5 | 99.4 | 99.95 |

Section 5.4. Validation Results

The performance of the LDA classifier was analyzed using each combination independently. Different K-fold cross validations were investigated using the study data set repeated 10 times for each procedure. A sample average performance of fivefold, sevenfold, and tenfold cross validations are shown below in Tables VIII, IX, and X respectively.

TABLE VIII

FIVEFOLD VALIDATION RESULTS OF THE PARAMETER COMBINATIONS (WINDOW SIZE = 5 SEC)

| Combination number | Combination parameters | Validation set (%) | | | |
|---|---|---|---|---|---|
|  |  | ACC | SE | P | AUC |
| #1 | QP, SP interval variability | 98.3 | 98.51 | 97.42 | 99.86 |
| #2 | QP, SP, RT interval variability | 98.37 | 98.601 | 98.1 | 99.89 |
| #3 | QP, SP, RT, TR interval variability | 98.16 | 98.5 | 98.84 | 99.84 |
| #4 | QP, SP, RT, TR, PQ interval variability | 98.8 | 98.74 | 98.54 | 99.90 |
| #5 | QP, SP, RT, TR, PQ, PS interval variability | 99.02 | 98.92 | 98.41 | 99.96 |

TABLE IX

SEVENFOLD VALIDATION RESULTS OF THE PARAMETER
COMBINATIONS (WINDOW SIZE = 5 SEC)

| Combination number | Combination parameters | Validation set (%) | | | |
|---|---|---|---|---|---|
| | | ACC | SE | P | AUC |
| #1 | QP, SP interval variability | 98.42 | 98.55 | 97.42 | 99.86 |
| #2 | QP, SP, RT interval variability | 98.45 | 98.65 | 98.13 | 99.89 |
| #3 | QP, SP, RT, TR interval variability | 98.26 | 98.59 | 98.84 | 99.85 |
| #4 | QP, SP, RT, TR, PQ interval variability | 98.83 | 98.80 | 98.60 | 99.91 |
| #5 | QP, SP, RT, TR, PQ, PS interval variability | 99.08 | 98.94 | 98.44 | 99.96 |

TABLE X

TENFOLD VALIDATION RESULTS OF THE PARAMETER
COMBINATIONS (WINDOW SIZE = 5 SEC)

| Combination number | Combination parameters | Validation set (%) | | | |
|---|---|---|---|---|---|
| | | ACC | SE | P | AUC |
| #1 | QP, SP interval variability | 98.50 | 98.54 | 97.38 | 99.87 |
| #2 | QP, SP, RT interval variability | 98.47 | 98.61 | 98.18 | 99.89 |
| #3 | QP, SP, RT, TR interval variability | 98.32 | 98.60 | 98.81 | 99.86 |
| #4 | QP, SP, RT, TR, PQ interval variability | 98.88 | 98.81 | 98.63 | 99.91 |
| #5 | QP, SP, RT, TR, PQ, PS interval variability | 99.1 | 98.95 | 98.39 | 99.97 |

The most accurate sample performance is indicated by the fifth combination with any K-fold cross validation values. An ACC of 99.02%, an SC of 98.92%, and a P of 98.41% were obtained by the fivefold cross validation. By increasing the number of folds to seven, the ACC, the SE, and the P were improved by 0.06%, 0.02%, and 0.03%, respectively. The tenfold cross validation achieved the most accurate overall results with an ACC of 99.1%, an SE of 98.95%, and a P of 98.39%. The AUC values for most of the combinations with any K-fold cross validations were substantial as well.

Figure 10A:
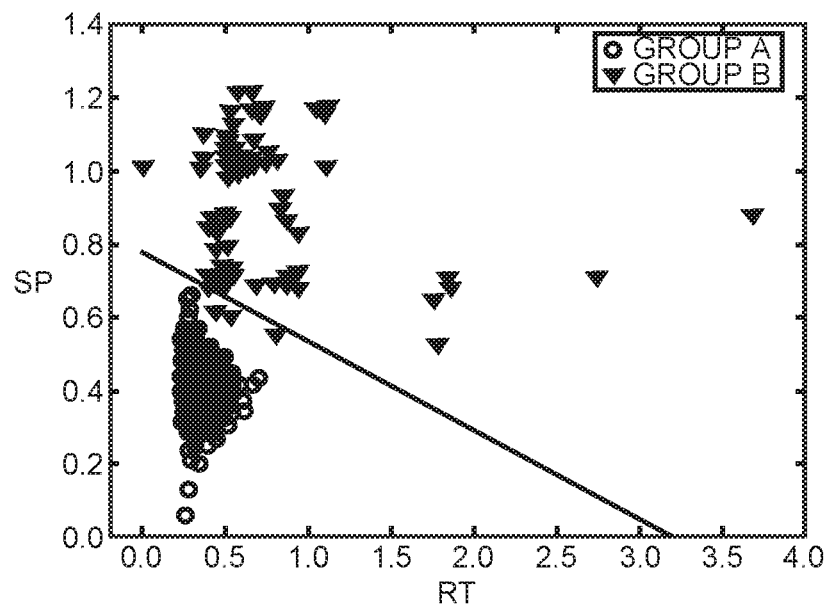
FIG. 10A is a scatter plot of the SP parameter versus the RT parameter.
Figure 10B:
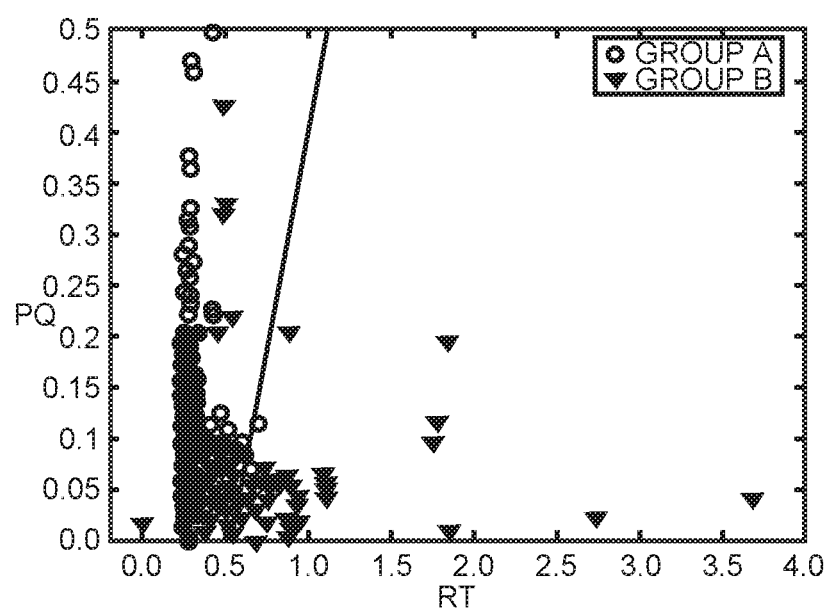
FIG. 10B is a scatter plot of the PQ parameter versus the RT parameter.
Figure 10C:
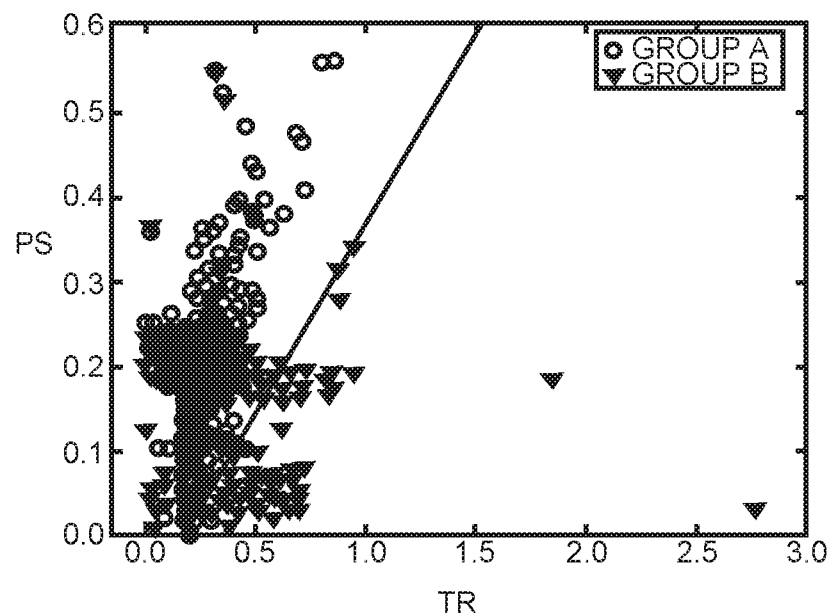
FIG. 10C is a scatter plot of the PS parameter versus the TR parameter.
Figure 10D:
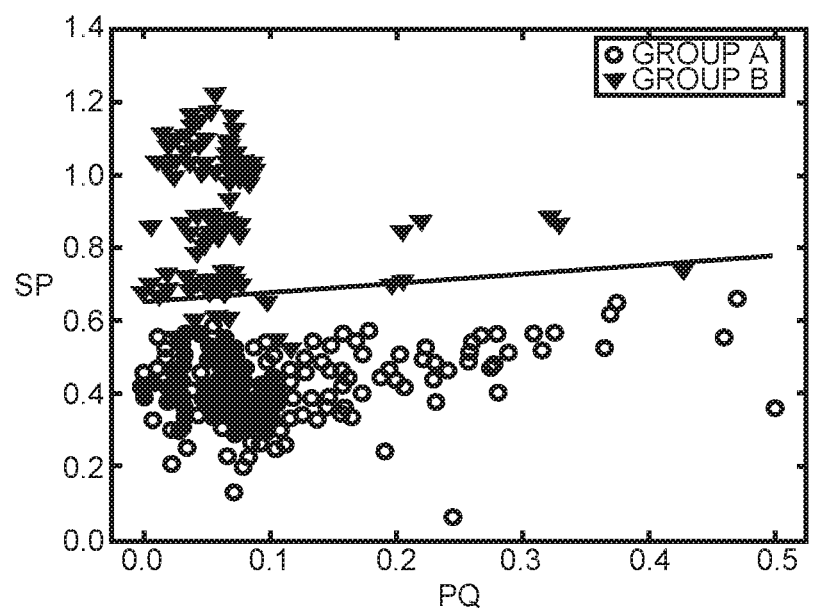
FIG. 10D is a scatter plot of the SP parameter versus the PQ parameter.
Figure 10E:
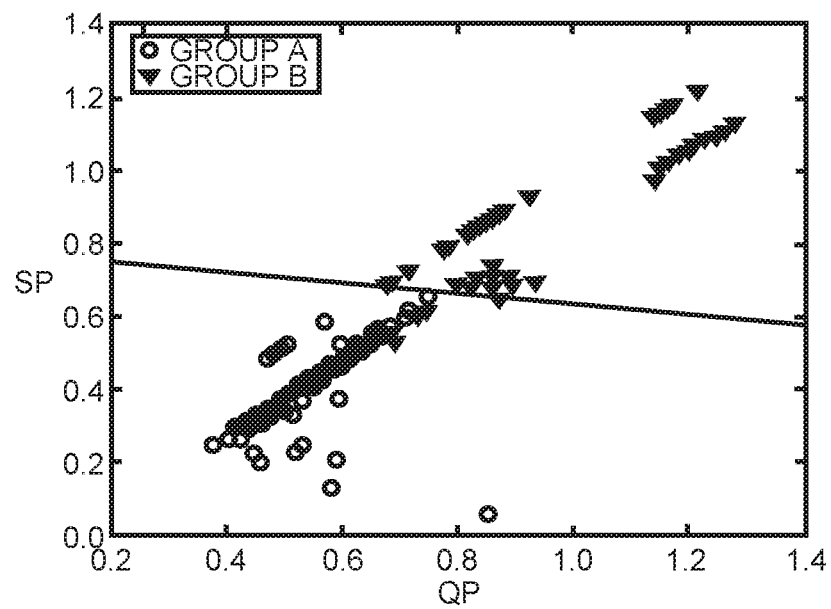
FIG. 10E is a scatter plot of the SP parameter versus the QP parameter.
Figure 10F:
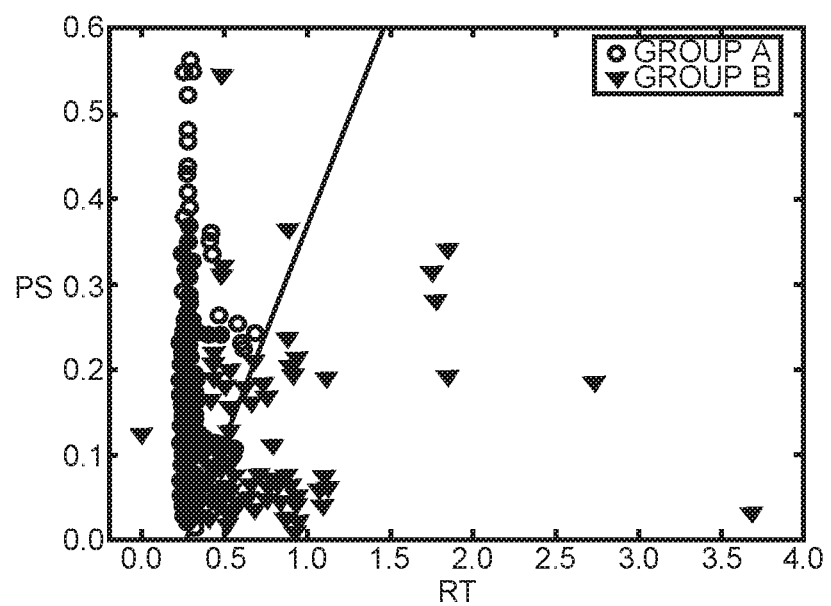
FIG. 10F is a scatter plot of the PS parameter versus the RT parameter.
Figure 10G:
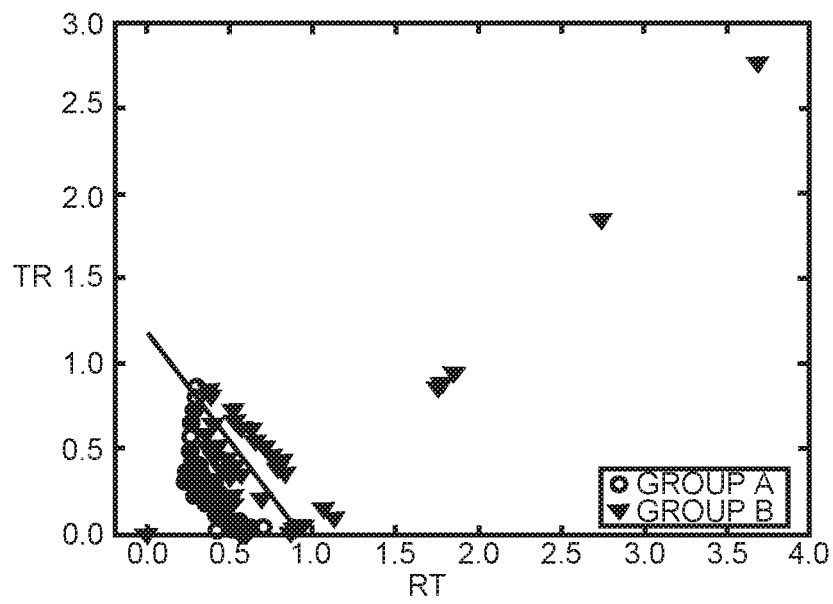
FIG. 10G is a scatter plot of the TR parameter versus the RT parameter.
Figure 10H:
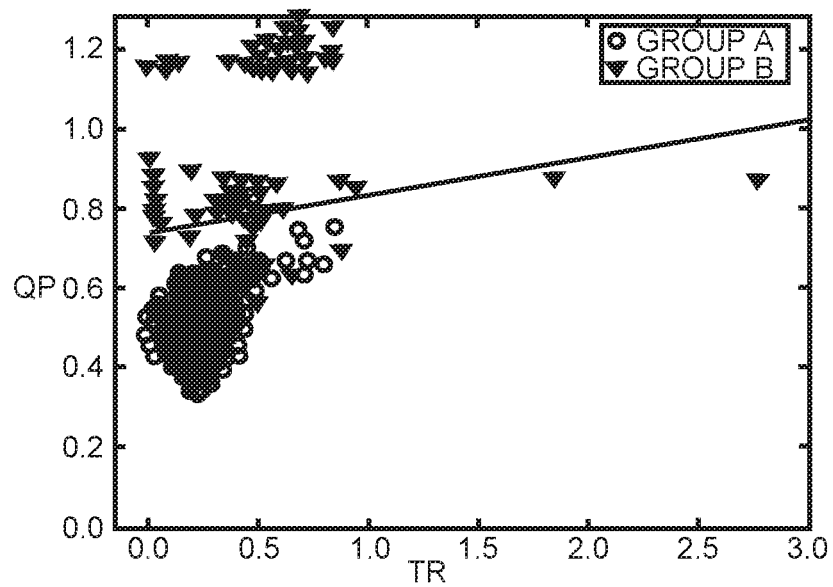
FIG. 10H is a scatter plot of the QP parameter versus the TR parameter.
Figure 10I:
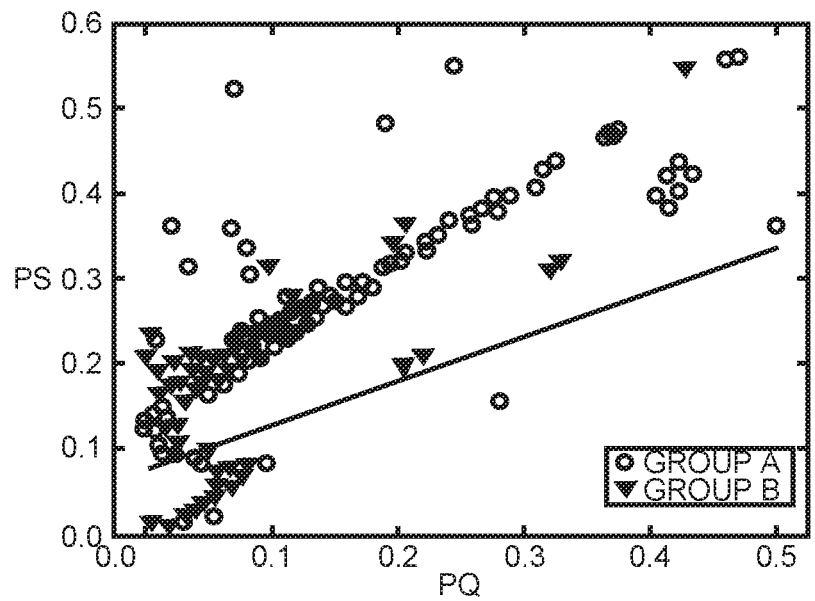
FIG. 10I is a scatter plot of the PS parameter versus the PQ parameter.
Figure 10J:
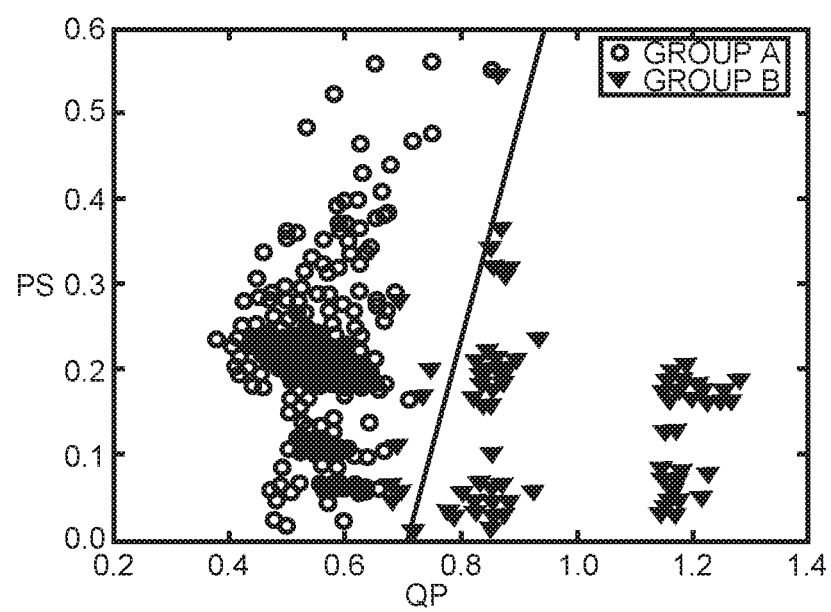
FIG. 10J is a scatter plot of the PS parameter versus the QP parameter.
Figure 10K:
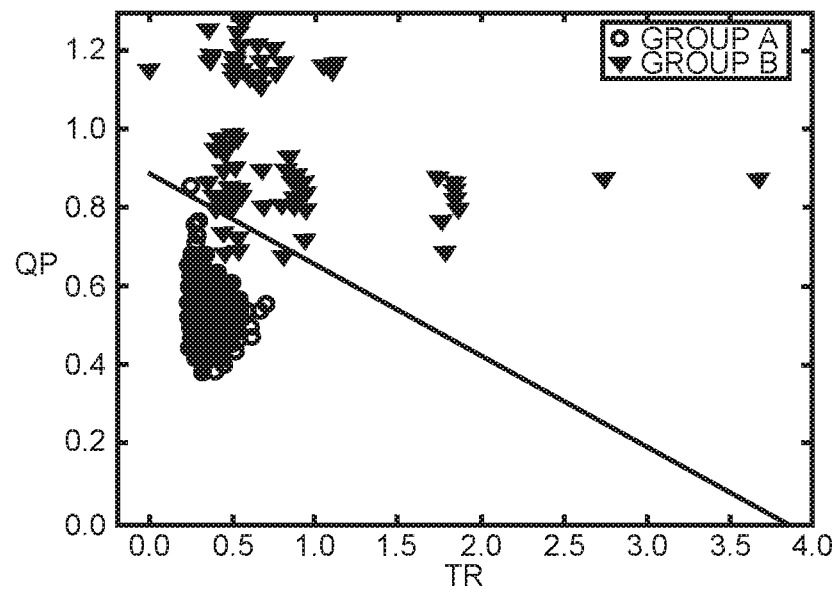
FIG. 10K is a scatter plot of the QP parameter versus the TR parameter.
Figure 10L:
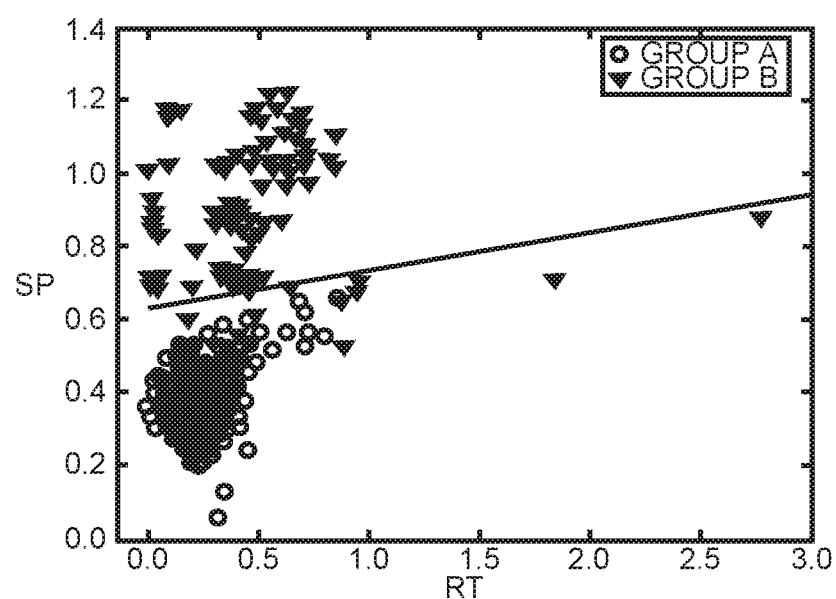
FIG. 10L is a scatter plot of the SP parameter versus the RT parameter.
Figure 10M:
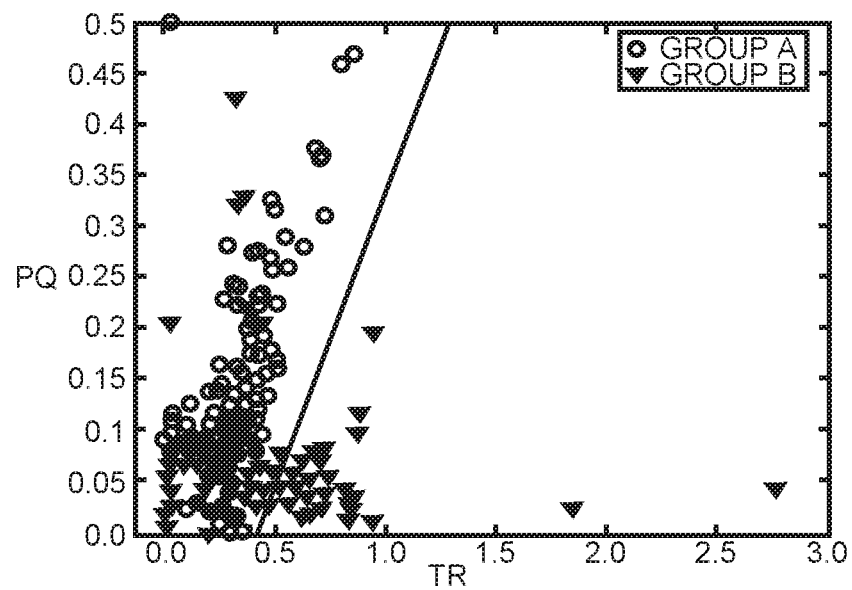
FIG. 10M is a scatter plot of the PQ parameter versus the TR parameter.
Figure 10N:
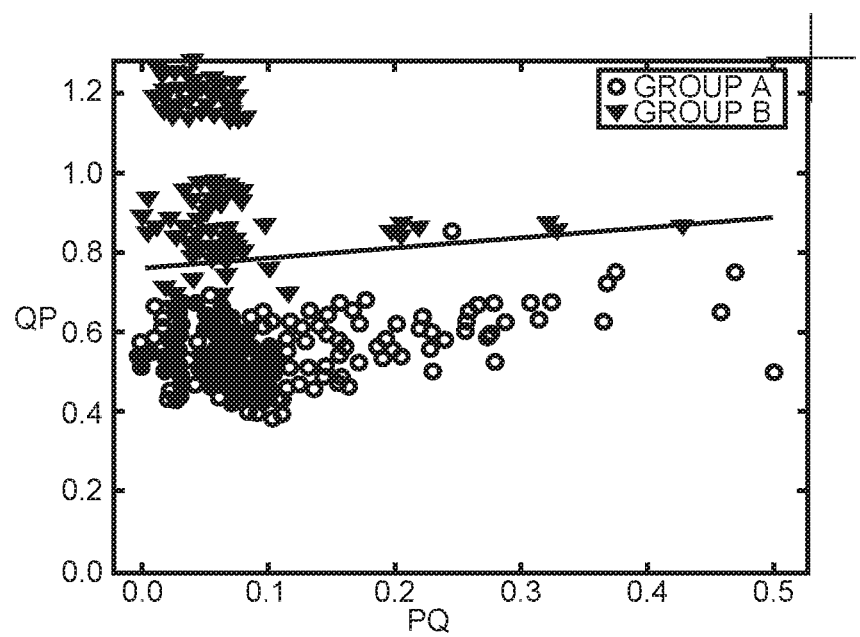
FIG. 10N is a scatter plot of the QP parameter versus the PQ parameter.
Figure 10O:
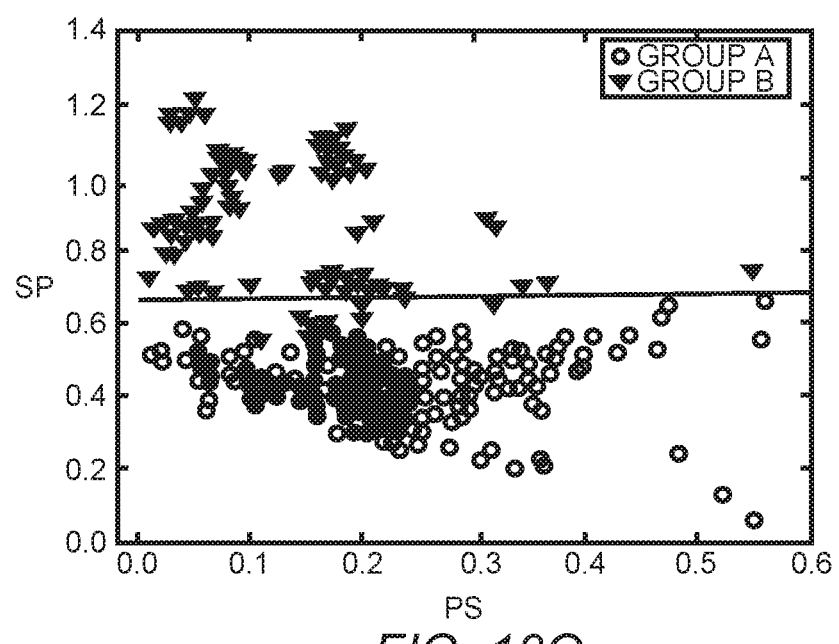
FIG. 10O is a scatter plot of the SP parameter versus the PS parameter.

FIGS. 10A through 10O are scatterplots for the ECG parameter pairs of the fifth combination using LDA for a tenfold cross validation. Note that the independency between most parameter pairs is substantial between GROUP A and GROUP B. The relatively strong delineation provided by LDA is graphically illustrated in FIGS. 10A through 10O considering the substantial separation between the GROUP A and the GROUP B parameter pairs.

Section 6. Conclusion

This disclosure provides the medical device 10 (FIG. 1), which is a new apparatus and detection method for determining a ventricular arrhythmia event. The medical device 10 combines a unique set of ECG parameters with the LDA algorithm. The six selected ECG parameters represent the status of two consecutive heartbeat signatures. To date, these six ECG parameters have not been used for ventricular arrhythmia detection. However, applicants of this disclosure discovered that each of these six new ECG parameters used by the medical device 10 provide unprecedented accuracy and efficiency for the detection of ventricular arrhythmia with a p-value that is less than 0.001.

While the QRS complex is detected using related-art techniques, such as PAT, a new P and T delineation technique is used to accurately and independently identify T waves and P waves. The new technique updates P wave and T wave delineation with each heartbeat based upon previously detected P waves and T waves. This delineation is achieved in the time domain without the need for spectral or transformation analysis of the ECG signal, which reduces the overall complexity of the medical device 10.

Moreover, the six ECG parameters are novel and include: PQ interval variability, QP interval variabilty, RT interval variability, TR interval variability, PS interval variability, and SP interval variability. The six ECG parameters are morphological, which provides benefits that include less processing time and fewer computations compared to traditional methods used to monitor for ventricular arrhythmia. Based upon statistical ROC analysis, the six ECG parameters individually and in combinations result in robust and accurate ventricular arrhythmia detection.

A Fisher LDA classifier is used to separate ventricular arrhythmia and non-ventricular arrthythmia. Despite the relative simplicity of the Fisher LDA, the differentiation between ventricular arrhythmia and non-ventricular arrthythmia is relatively high in comparison to traditional techniques used to differentiate between ventricular arrhythmia and non-ventricular arrthythmia. This relatively strong performance is not attributable to the Fisher LDA, but is rather attributable to the relevance between the six ECG parameters and their correlation to differences between ventricular arrhythmia and non-ventricular arrthythmia.

Those skilled in the art will recognize improvements and modifications to the embodiments of the present disclosure. All such improvements and modifications are considered within the scope of the concepts disclosed herein and the claims that follow.

What is claimed is:

1. A method for a medical device for detecting a ventricular arrhythmia event comprising:
   receiving by input circuitry of the medical device an electrocardiogram (ECG) signal;
   locating by processing circuitry of the medical device three or more QRS complexes within the ECG signal;
   locating by the processing circuitry R peaks within the three or more QRS complexes;
   determining by the processing circuitry a Q onset and a S offset;
   determining by the processing circuitry an RR interval between consecutive R peaks;
   determining by the processing circuitry search window boundaries between which a T wave and a P wave are located based upon the RR interval;
   providing by the processing circuitry a calculated T wave amplitude threshold and a calculated P wave amplitude threshold;
   determining by the processing circuitry a T wave location within the search window boundaries based upon the calculated T wave amplitude threshold;
   determining by the processing circuitry a P wave location within the search window boundaries based upon the calculated P wave amplitude threshold;
   extracting fiducial points by a fiducial point extraction block, wherein the fiducial points include at least a peak of the P wave location, the Q onset, and the S offset; and
   determining by feature extraction circuitry coupled to the fiducial point extraction block interval variabilities between the fiducial points, wherein the interval variabilities include a combination of QP interval variability and SP interval variability.

2. The method for the medical device of claim 1 further including detecting by machine learning circuitry ventricular arrhythmia based upon the interval variabilities determined by the feature extraction circuitry.

3. The method for the medical device of claim 2 wherein the interval variabilities are further selected from the group consisting of RT interval variability, TR interval variability, PQ interval variability, and PS interval variability.

4. The method for the medical device of claim 1 wherein a T wave fiducial point is a peak of the T wave at the T wave location determined by a T wave delineation block.

5. The method for the medical device of claim 1 wherein the peak of the P wave at the P wave location is determined by a P wave delineation block.

6. The method for the medical device of claim 5 wherein other fiducial points are selected from the group consisting of P offset, R peak, and T offset.

7. The method for the medical device of claim 1 further comprises:
taking by the processing circuitry a derivative of a filtered ECG signal received by the input circuitry;
squaring by the processing circuitry the derivative of the filtered ECG signal; and
integrating by the processing circuitry a square of the derivative of the filtered ECG signal for a duration of at least two heartbeat cycles.

8. The method for the medical device of claim 1 further including removing, by the input circuitry, unwanted noise signals mixed with a received ECG signal.

9. A medical device for detecting a ventricular arrhythmia event comprising:
input circuitry configured to receive an electrocardiogram (ECG) signal;
processing circuitry coupled to the input circuitry and comprising:
a QRS complex demarcation block configured to locate three or more consecutive QRS complexes within the ECG signal;
an R peak detection block configured to locate R peaks within the located QRS complexes;
a Q onset and S offset block configured to determine a Q onset and an S offset;
an RR demarcation block configured to determine an RR interval between consecutive R peaks located by the R peak detection block;
a search windows calculator block configured to determine search window boundaries between which a T wave and a P wave are located based upon the RR interval;
a T and P wave thresholds calculator block configured to provide a calculated T wave amplitude threshold and a calculated P wave amplitude threshold;
a T wave delineation block configured to determine a T wave location within the search window boundaries based upon the calculated T wave amplitude threshold;
a P wave delineation block configured to determine a P wave location within the search window boundaries based upon the calculated P wave amplitude threshold;
a fiducial point extraction block configured to extract fiducial points within the search window boundaries, wherein the fiducial points include at least the P wave location, the Q onset and the S offset; and
feature extraction circuitry coupled to the fiducial point extraction block and configured to determine interval variabilities between the fiducial points, wherein the interval variabilities include a combination of QP interval variability and SP interval variability.

10. The medical device of claim 9 further including machine learning circuitry configured to detect ventricular arrhythmia based upon the interval variabilities determined by the feature extraction circuitry.

11. The medical device of claim 9 wherein the interval variabilities are further selected from the group consisting of RT interval variability, TR interval variability, PQ interval variability, and PS interval variability.

12. The medical device of claim 9 wherein a T wave fiducial point is a peak of the T wave at the T wave location determined by the T wave delineation block.

13. The medical device of claim 9 wherein a P wave fiducial point is a peak of the P wave at the P wave location determined by the P wave delineation block.

14. The medical device of claim 13 wherein other fiducial points are selected from the group consisting of P offset, Q onset, R peak, S offset, and T offset.

15. The medical device of claim 9 wherein the processing circuitry further comprises:
a differentiation block coupled to an output of the input circuitry and configured to take a derivative of a filtered ECG signal;
a squaring block coupled to an output of the differentiation block and configured to square the derivative of the filtered ECG signal; and
a moving window integral block coupled between an output of the squaring block and an input of the QRS complex demarcation block, wherein the moving window integral block is configured to integrate the square of the derivative of the filtered ECG signal for a duration of at least two heartbeat cycles.

16. The medical device of claim 9 wherein the input circuitry includes at least one filter configured to remove unwanted noise signals mixed with a received ECG signal.

* * * * *

UNITED STATES PATENT AND TRADEMARK OFFICE
CERTIFICATE OF CORRECTION

PATENT NO. : 10,548,499 B2
APPLICATION NO. : 15/616069
DATED : February 4, 2020
INVENTOR(S) : Nourhan Yahya Bayasi et al.

Page 1 of 1

It is certified that error appears in the above-identified patent and that said Letters Patent is hereby corrected as shown below:

In the Claims

Claim 3, Column 17, Line 7, replace "The method for the medical device of claim 2" with --The method for the medical device of claim 1--.

Claim 14, Column 18, Lines 34-35, replace "the group consisting of P offset, Q onset, R peak, S offset, and T offset" with --the group consisting of P offset, R peak, and T offset--.

Signed and Sealed this
Second Day of June, 2020

Andrei Iancu
*Director of the United States Patent and Trademark Office*